(12) United States Patent  
Burnet et al.

(10) Patent No.: US 9,145,436 B2
(45) Date of Patent: Sep. 29, 2015

(54) ANTI-INFLAMMATORY MACROLIDES

(76) Inventors: Michael W. Burnet, Tuebingen (DE); Jan-Hinrich Guse, Tibingen-Buhl (DE); Christiane Bauerlein, Ofterdingen (DE); Mary Eggers, Ammerbuch (DE)

(*) Notice: Subject to any disclaimer, the term of this patent is extended or adjusted under 35 U.S.C. 154(b) by 5 days.

(21) Appl. No.: 13/878,751

(22) PCT Filed: Oct. 10, 2011

(86) PCT No.: PCT/US2011/055657
§ 371 (c)(1),
(2), (4) Date: Sep. 12, 2013

(87) PCT Pub. No.: WO2012/051126
PCT Pub. Date: Apr. 19, 2012

(65) Prior Publication Data
US 2014/0031307 A1     Jan. 30, 2014

Related U.S. Application Data

(60) Provisional application No. 61/391,679, filed on Oct. 10, 2010.

(51) Int. Cl.
*A61K 31/70* (2006.01)
*C07H 17/08* (2006.01)

(52) U.S. Cl.
CPC ........................... *C07H 17/08* (2013.01)

(58) Field of Classification Search
CPC ........................................................ C07H 17/08
See application file for complete search history.

(56) References Cited

U.S. PATENT DOCUMENTS

| | | | |
|---|---|---|---|
| 6,936,592 B2 * | 8/2005 | Bronk et al. ............... | 514/29 |
| 7,767,797 B1 | 8/2010 | Gutke et al. | |
| 2004/0014952 A1 | 1/2004 | Rengaraju | |
| 2004/0097434 A1 | 5/2004 | Mercep et al. | |
| 2004/0186063 A1 | 9/2004 | Gutke et al. | |
| 2006/0069047 A1 | 3/2006 | Burnet et al. | |
| 2009/0131343 A1 | 5/2009 | Phan et al. | |
| 2009/0221697 A1 | 9/2009 | Laufer et al. | |
| 2010/0197622 A1 | 8/2010 | Oyelere | |

FOREIGN PATENT DOCUMENTS

| | | |
|---|---|---|
| GB | 2 327 084 A | 1/1999 |
| WO | WO-99/00125 A1 | 1/1999 |
| WO | WO-99/20639 A2 | 4/1999 |
| WO | WO-03/070174 A2 | 8/2003 |

OTHER PUBLICATIONS

Mencarelli et al., "Development of non-antibiotic macrolide that corrects inflammation-driven immune dysfunction in models of inflammatory bowel diseases and arthritis", European Journal of Pharmacology, vol. 665, No. 1-3, pp. 29-39 (Apr. 2011).
Supplemental European Search Report dated Feb. 24, 2014, in corresponding European Patent Application No. 11833216.2.
International Search Report dated May 30, 2012, from corresponding PCT Application Serial No. PCT/US11/55657.
Written Opinion dated May 30, 2012, from corresponding PCT Application Serial No. PCT/US11/55657.

* cited by examiner

*Primary Examiner* — Elli Peselev
(74) *Attorney, Agent, or Firm* — Locke Lord LLP; Jeffrey D. Hsi

(57) ABSTRACT

The invention provides novel compounds and compositions and methods for making and using the compounds and compositions.

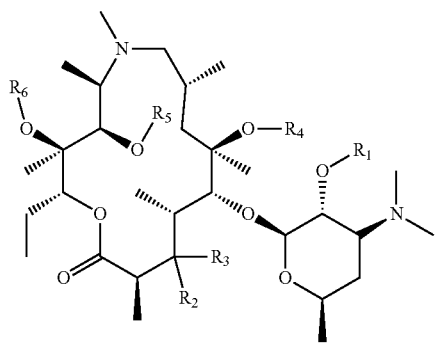

8 Claims, 18 Drawing Sheets

Figure 1. Generic structure for the descladinosyl macrolides
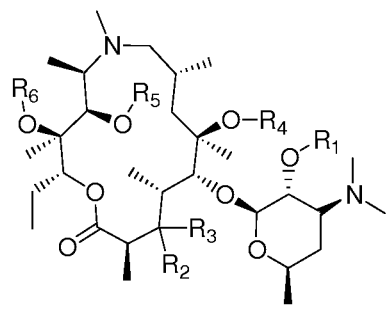
Figure 2. Compound 2 depicted as the oxidized version and the corresponding hemiketal structure.
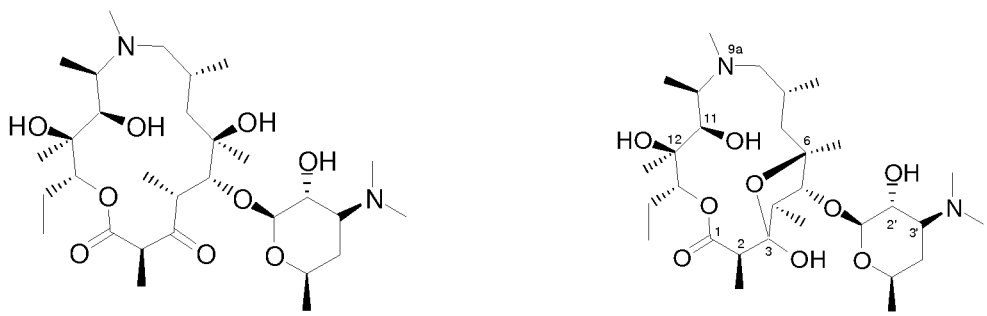

Figure 3. Compound 3, Azithromycin
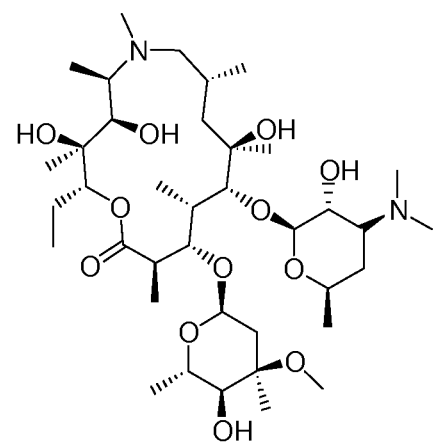

Figure 4. Change in score following induction of collagen induced arthritis in DBA mice treated either with the compound 2, or vehicle (1% citrate)
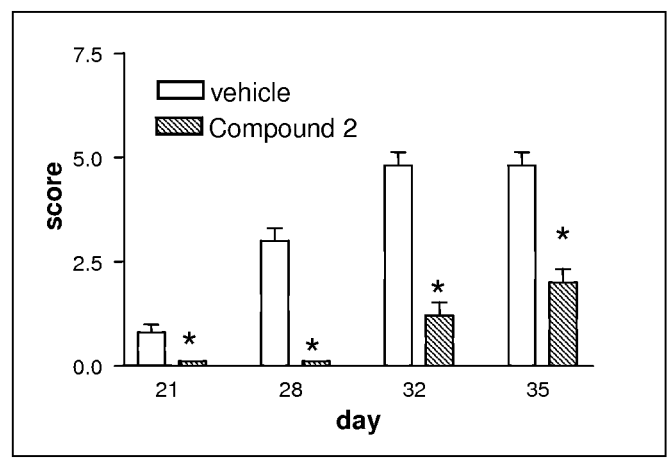

Figure 5. Diarrhea severity in mice in which colitis has been induced using DSS and which have subsequently been treated with either Compound 2 or the controls sulfasalazine or its Vehicle Saline or DMSO/1% carboxymethylcellulose or the well known anti-inflammatory kinase inhibitor SB203580.
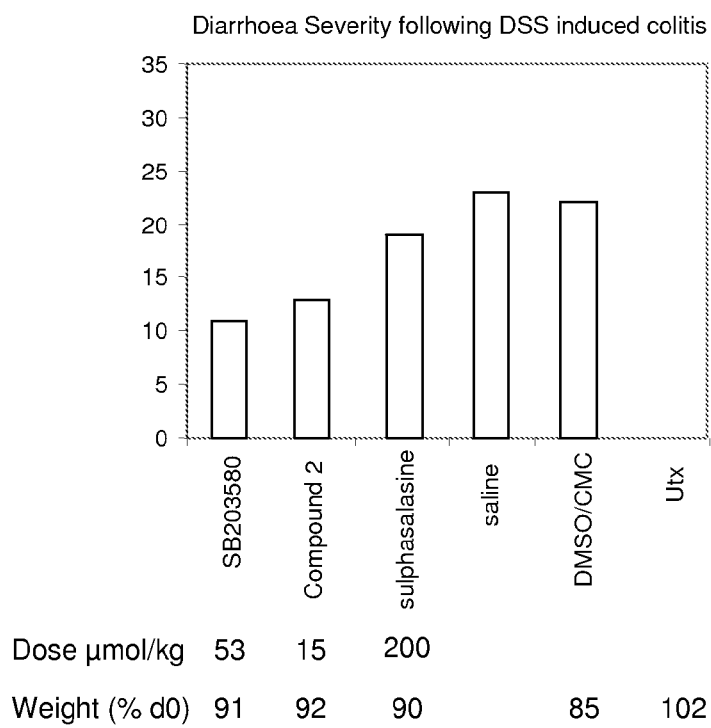

Figure 6. Histological severity in mice in which colitis has been induced using DSS and which have subsequently been treated with either Compound 2 or the controls sulfasalazine or its Vehicle Saline or DMSO/1% carboxymethylcellulose or the well known anti-inflammatory kinase inhibitor SB203580.
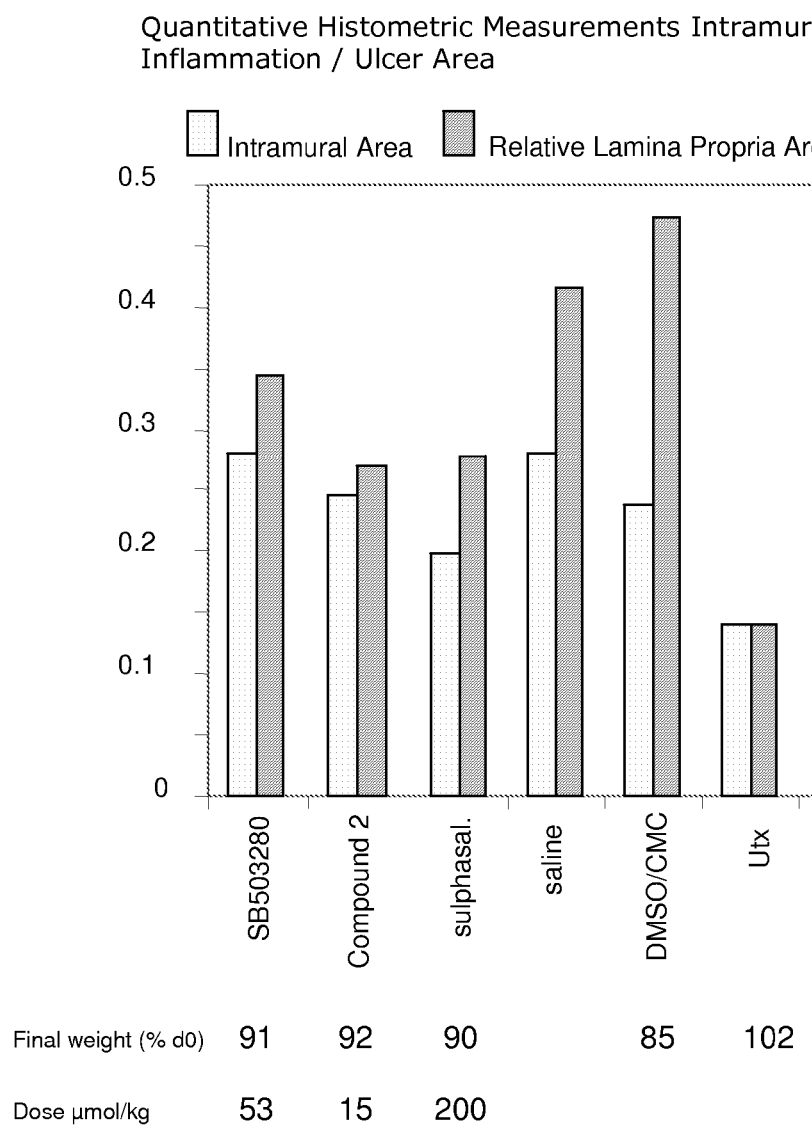

Figure 7. Diarrhea severity in mice in which colitis has been induced using TNBS and which have subsequently been treated with either Compound 2 or the Vehicle (indicated as "TNBS" or Saline instead of TNBS.
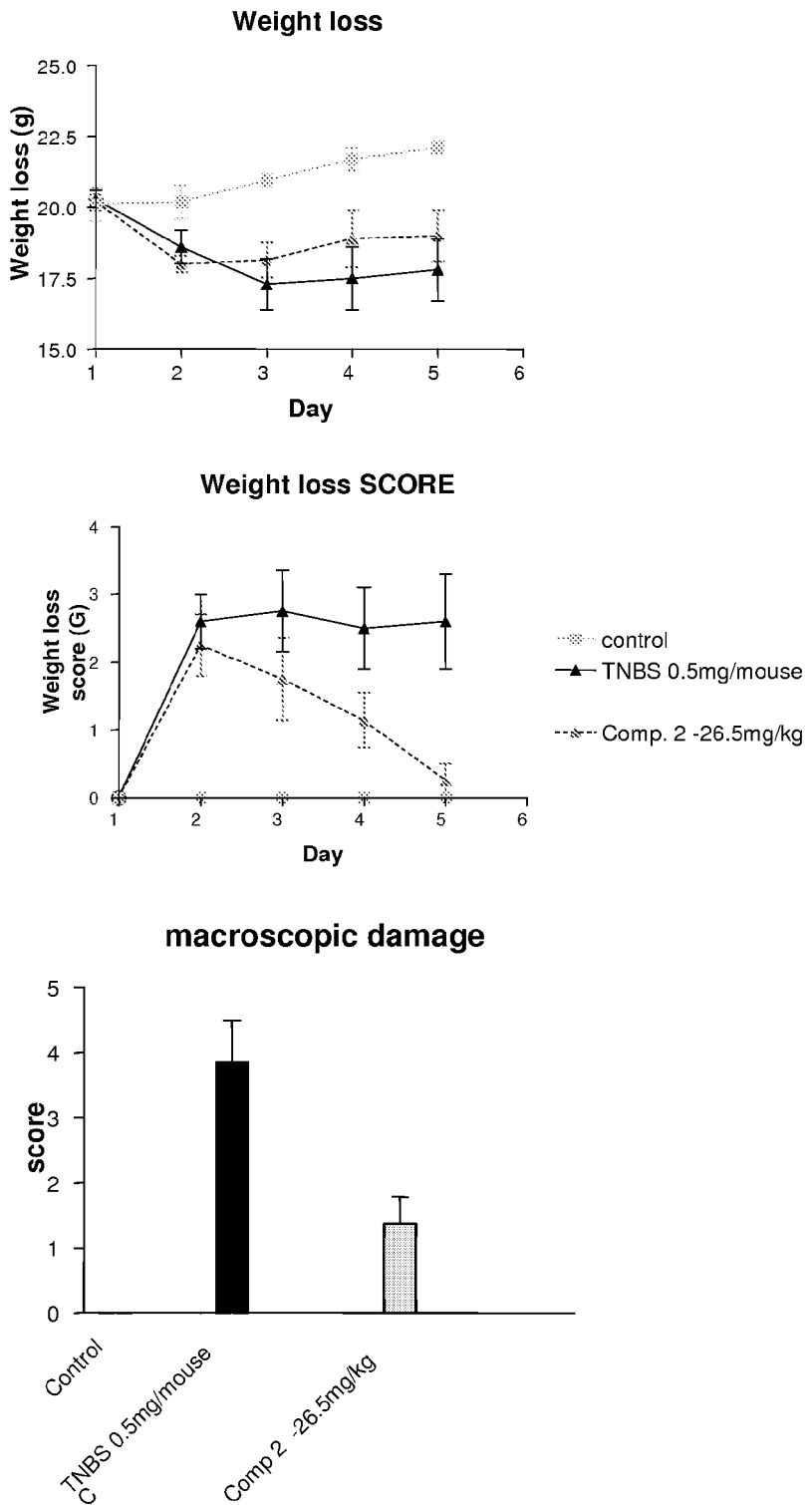

Figure 8. Compound 6
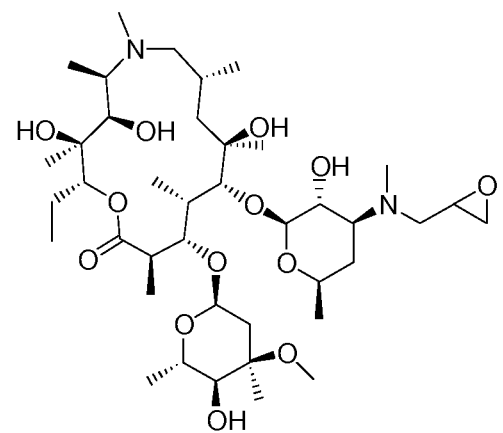
Figure 9. Compound 7
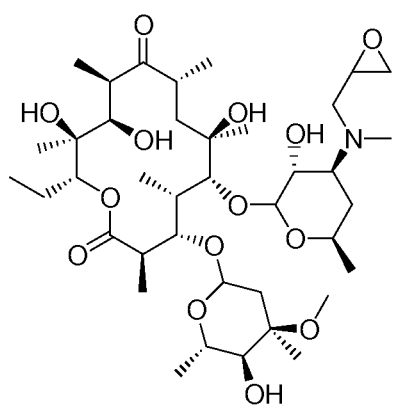

Figure 10. Weight change in mice in which colitis has been induced using DSS and which have subsequently been treated with either Compound 2, Compound 3, Compound 6 Erythromycin or the controls sulfasalazine or its Vehicle (DSS Only).
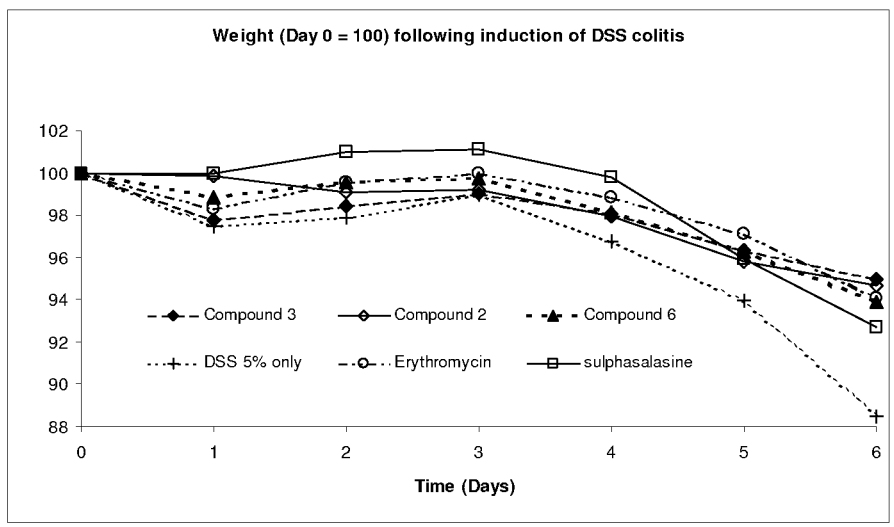

Figure 11. Weight change in mice in which colitis has been induced using DSS and which have subsequently been treated with either Compound 2, Compound 4 the controls sulfasalazine or its Vehicle in comparison with mice in which no disease has been induced.
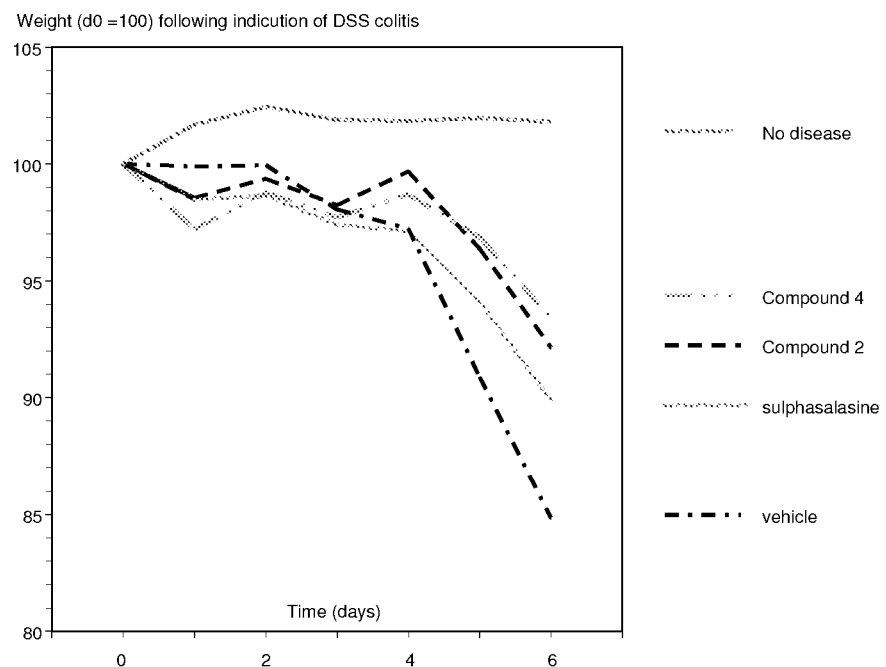

Figure 12. Plasma TNFa production in Lewis rats in which liver damage is induced via injection of LPS (4 mg/kg), data are the mean of N=8 and are plotted with the 95% confidence interval.
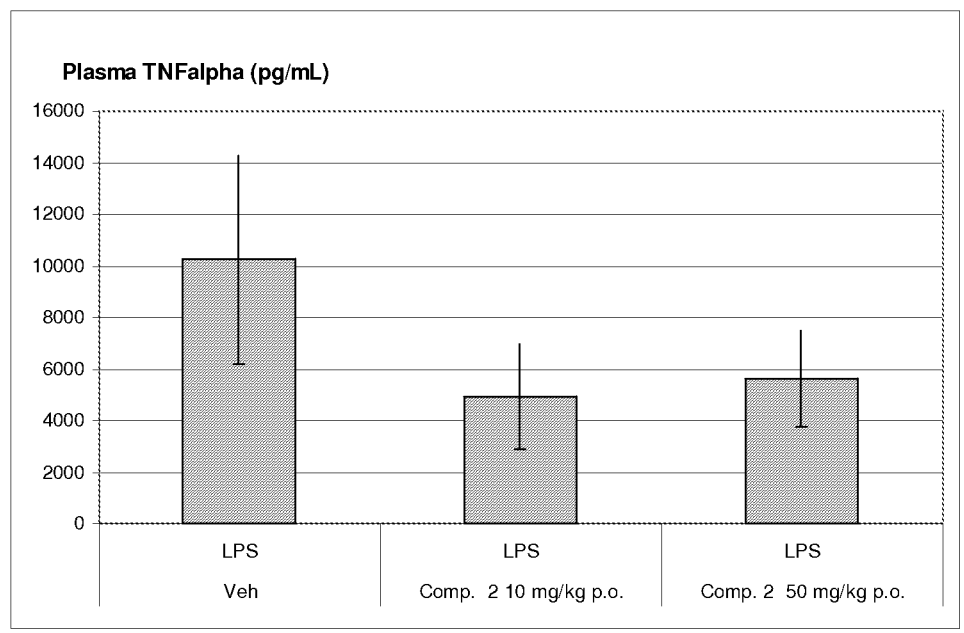

Figure 13. TNFa concentration in Bronchoalveolar lavage fluid following aspiration of LPS into the lung. Mice were treated either orally (p.o.) or intranasally (i.n.)
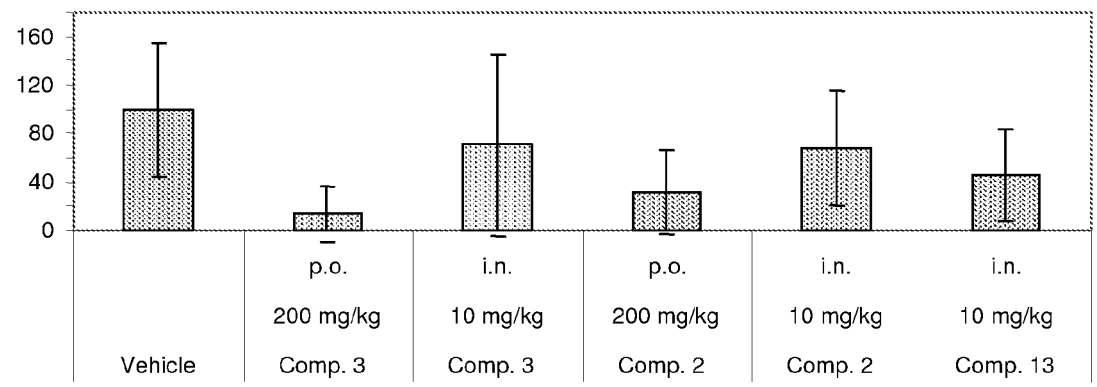

Figure 14. Examples of Compound 2 Derivatives shown as the oxidized form.
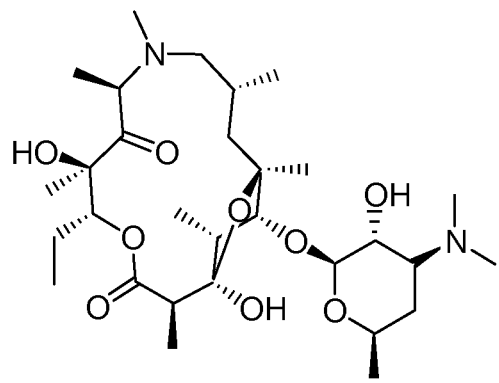
Compound 4
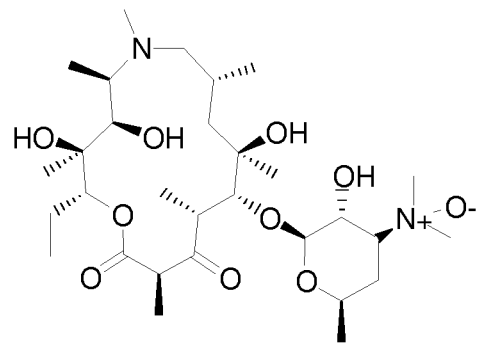
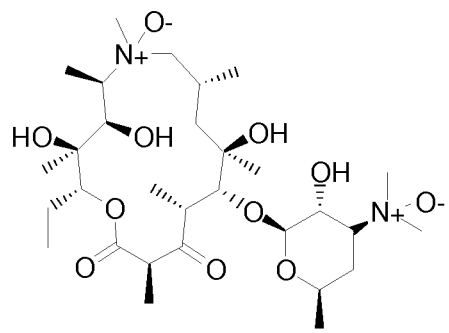
Compound 5a  Compound 5b Figure 14. (cont.)
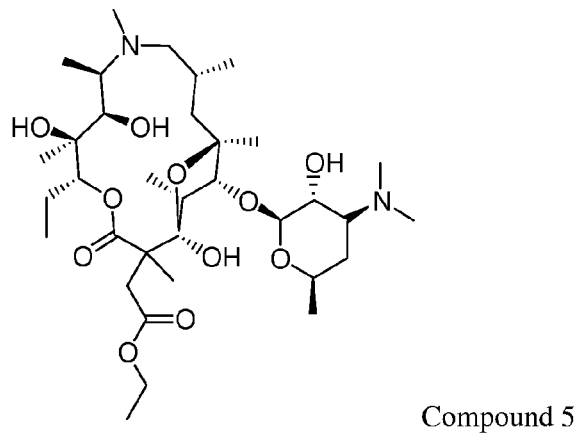
Compound 5
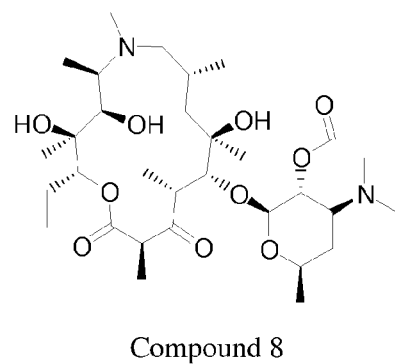
Compound 8
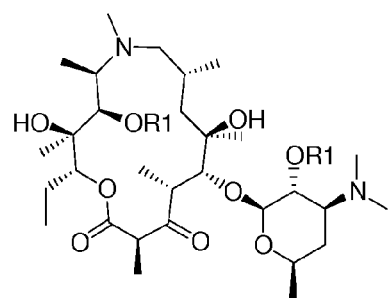
R1 = oleic ester
Compound 9
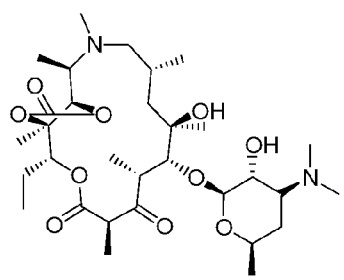
Compound 10

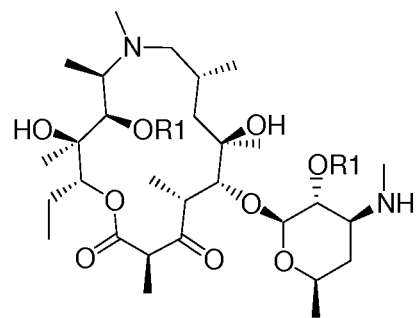
Compound 11
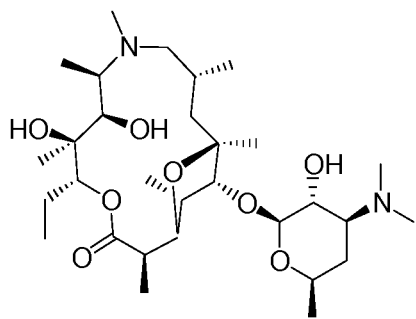
Compound 13
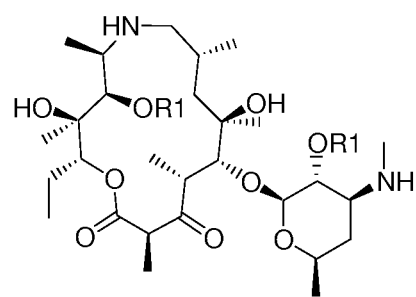
Compound 14
Figure 14. (cont.)

Figure 15. Effect of compound 2 on hERG currents in hERG expressing cells relative to compound 3.
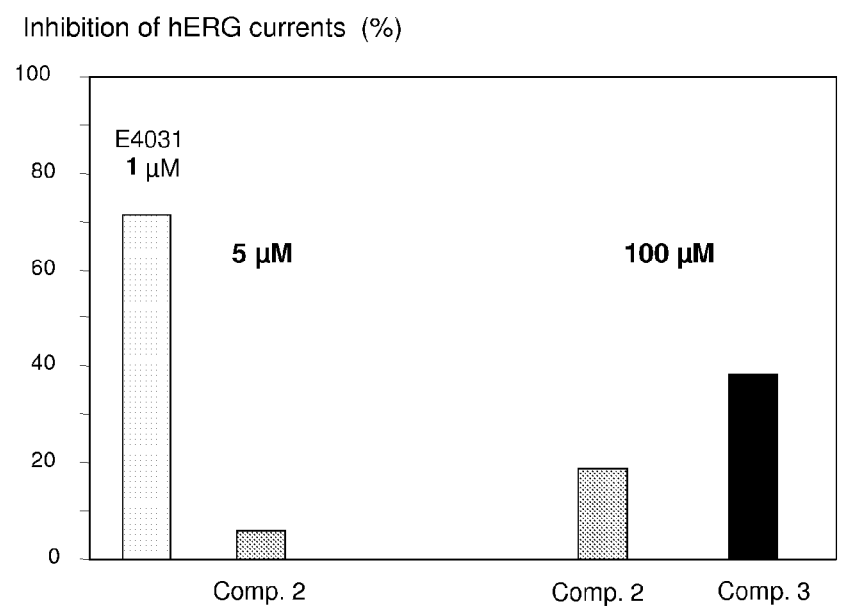

Figure 16. Effect of compound 2 or compound 3 on the growth of E. coli or B. pumulius in liquid medium.
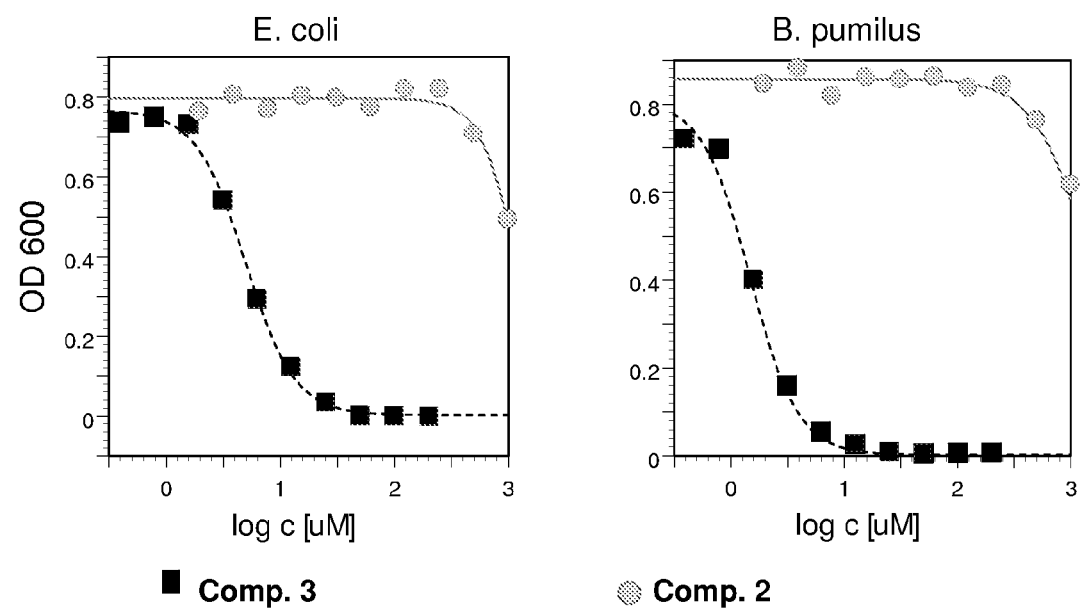

Figure 17. Effect of compound 2 on the growth of juvenile mice when given p.o. at 400 μmol/kg.
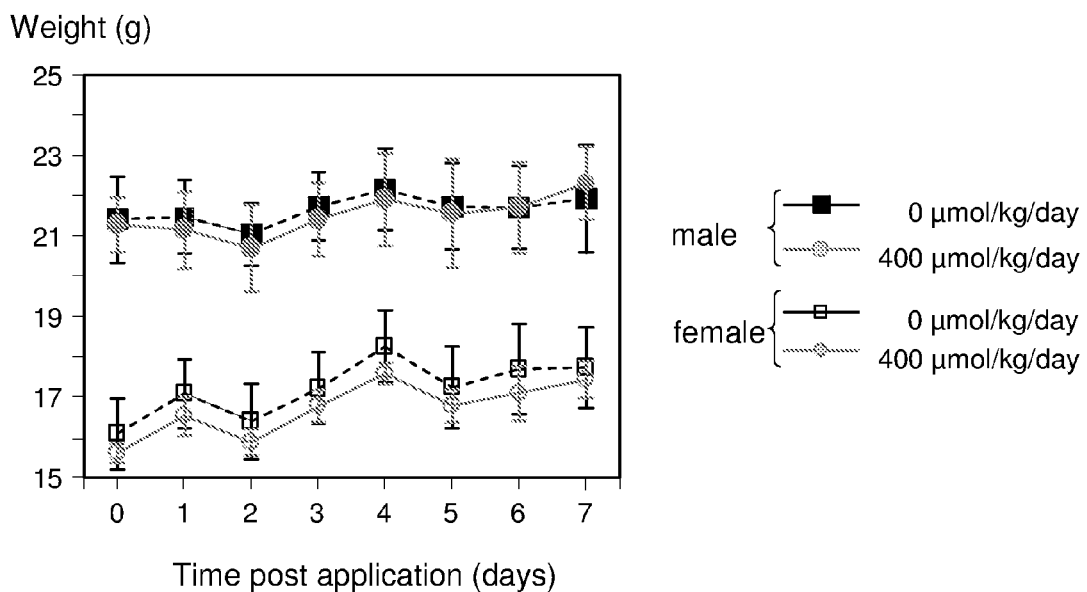
Figure 18. Effect of compound 2 or 3 on the normal gut flora of mice when given p.o. at 45 μmol/kg.
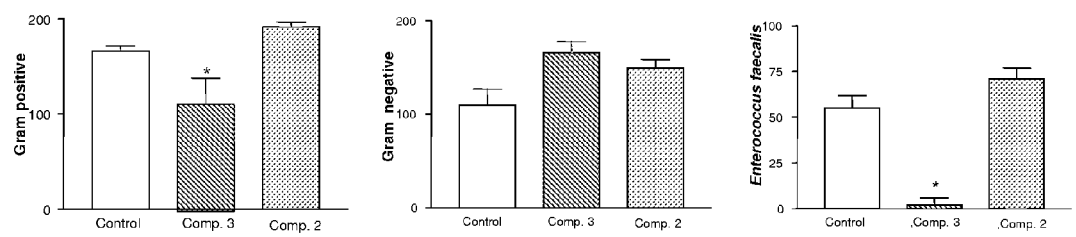

Figure 19. Mass spectrum of COMPOUND 2 (the high background is due to the low sample concentration).
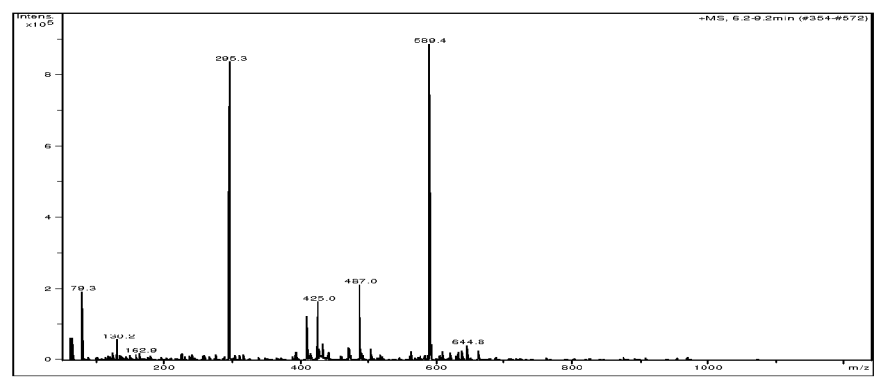
Figure 20. Fragment mass spectrum of COMPOUND 2 m/z 589.5 adduct mass.
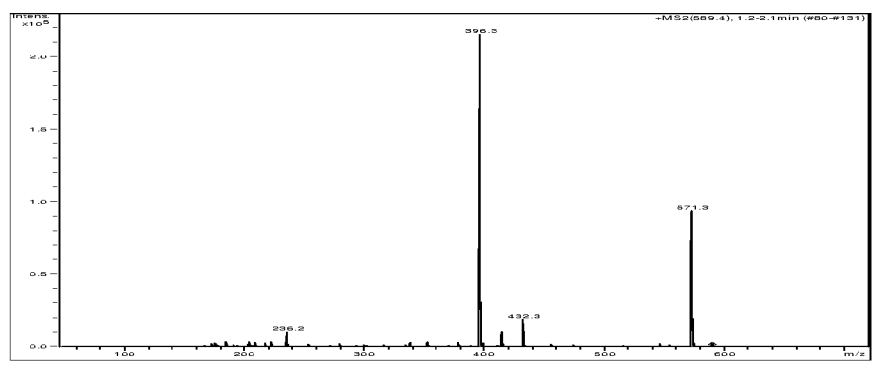

ANTI-INFLAMMATORY MACROLIDES

RELATED APPLICATIONS

This application is the national stage application pursuant to 35 U.S.C. §371 of PCT application PCT/US2011/055657, filed Oct. 10, 2011, which claims priority to U.S. Provisional Application No. 61/391,679, filed Oct. 10, 2010. The contents of each of the foregoing applications are incorporated herein by reference in their entirety.

BACKGROUND

Macrocyclic lactones, and in particular, the "macrolides" are naturally derived and semi-synthetic compounds with a range of biological activities. Amongst the best known of these activities is antibiotic activity through binding to the bacterial ribosome. Certain of these compounds do, however, have other activities including anti-inflammatory activity (see European patent publication 0283055). In recent years, macrocycles may have been used as drug carriers in which an active substance is reversibly bonded to the macrocycle via an ester bond (see, e.g., PCT Publication 03/070174). However, remaining antibiotic activity of the macrocycle has the attendant danger of promoting bacterial resistance to this drug class amongst the patient population.

Various observations have linked bacterial resistance to macrocycles to either mutation of the ribosome subunits, or up-regulation of efflux processes (see Douthwaite et al., J. Antimicrob. Chemother. (2001) 48 (suppl 2): 1-8, for review, and Bonnefoy, et al., J. Antimicrob. Chemother. (1997) 40 (1): 85-90). The efflux systems in a range of bacteria are considered to recognize in part the so-called "cladinose" sugar found in the erythromycin derived macrocycles. Removal of this sugar therefore means the potential of reducing the capacity for a macrocyclic compound to stimulate non-specific antibiotic resistance.

Although cladinose is part of the efflux recognition motif, there are a number of anti-bacterial molecules, the so-called ketolides, that have either no cladinose group, or a modification at the cladinose position. Thus, decladinosyl species are not intrinsically non-antibacterial and decladinosyl azithromycin is ca. 5-fold less effective than the cladinosylated molecule. However, it would be desirable to provide a compound having anti-inflammatory activity and at the same time, complete or at least partial elimination of antibiotic activity, e.g., at least one hundred-fold or more less effective as antibiotics, in order to avoid imposing selection pressure for resistance.

Various workers have attempted to design such molecules. The most common approach is based on the idea of sterically blocking the site that interacts with the target bacterial ribosome. For example, the hydroxyl and amine groups on the desosamine ring are the main interactors with the ribosome and reaction at these sites with bulky groups reduces antibacterial activity. However, addition of bulky groups to this position, while facile, leads to larger molecules which are intrinsically less suitable as pharmaceuticals because their large size make them more likely to interact with non-target receptors.

A large number of researchers have reported derivatives of macrocycles (see, e.g., Elliot et al., 1998, J. Med. Chem. 41, 1651-1659); however, these derivatives have typically been limited to substitutions on the macrolactone ring or modifications of the sugar residues (cladinose to carbonyl for example in the case of the ketolides). Working on methylated macrocycles, Kobrehel et al. (U.S. Pat. No. 6,369,035) reported intermediates following oxidation with ketolide-like properties as antimicrobial compounds.

SUMMARY OF THE INVENTION

In one aspect, the invention relates to a compound of the following formula:

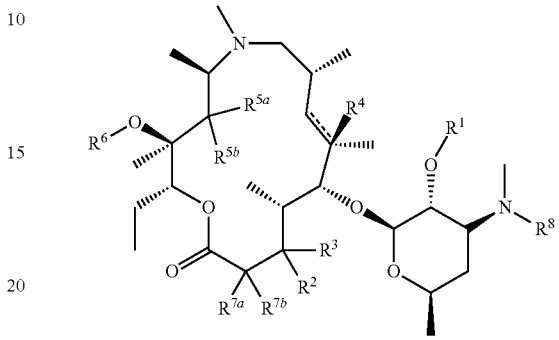

Wherein:
The dashed line represents an optional bond;
$R^1$ and $R^8$ are each independently H;
$(C_1$-$C_{10})$alkyl;
$(C_2$-$C_{10})$alkenyl;
$(C_2$-$C_{10})$alkynyl;
$(C_1$-$C_8)[(C_1$-$C_4)$alkoxy]alkyl;
$(C_2$-$C_8)[(C_1$-$C_4)$alkoxy]alkenyl;
$(C_6$-$C_{10})$aryl-$(C_1$-$C_5)$alkyl;
$(C_2$-$C_9)$heteroaryl-$(C_1$-$C_5)$alkyl;
$(C_1$-$C_4)$alkyliden-$NR^{18}R^{19}$;
$C(=O)$—Y—$R^{15}$;
$C(=O)$—$R^{15}$;
$S(=O)_k(C_1$-$C_{10})$alkyl;
$S(=O)_k(C_1$-$C_{10})$alkenyl;
$S(=O)_k(C_1$-$C_{10})$alkynyl;
$S(=O)_k(C_6$-$C_{10})$aryl;
$S(=O)_k(C_2$-$C_9)$heteroaryl;
$S(=O)_k$;
$(C=O)(CH_2)_kCOO(CH_2)_kH$;
$NO_2$ (only for $R^1$); or
$(C=O)(CH_2)_kO(CH_2)_{k'}COO(CH_2)_kH$;
wherein k and k' are each independently 0, 1 or 2; l is 0, 1 or 2, and alkyl, alkenyl, alkynyl, cycloalkyl, heterocycloalkyl, aryl and heteroaryl can optionally be substituted by one to three halogen, cyano, hydroxy, $(C_1$-$C_4)$alkyloxy, nitro, $(C_1$-$C_6)$alkyl, $(C_1$-$C_6)$alkenyl, $(C_1$-$C_6)$alkynyl, $(C_3$-$C_7)$cycloalkyl, $(C_1$-$C_6)$heterocycloalkyl, $(C_6$-$C_{10})$aryl, $(C_1$-$C_9)$heteroaryl, $NR^{18}R^{19}$, $R^{18}C(=O)$—, $R^{18}C(=O)O$—, $R^{18}OC(=O)$—, $R^{18}C(=O)NH$—, $R^{18}NHC(=O)$—, $R^{18}R^{19}NC(=O)$— or $R^{18}OC(=O)$—O—;
$R^2$ and $R^3$=—OH (provided that only one of $R^2$ and $R^3$ is OH);
or $R^2$ and $R^3$ taken together are (=O) or (=$NR^1$);
$O(CH_2)_kO$—, wherein k is 2 or 3;
$O(C=O)(CH_2)_kCOO(CH_2)_kH$; or
$O(C=O)(CH_2)_kO(CH_2)_{k'}COO(CH_2)_kH$
or $R^2$=OH, and $R^3$ and $R^4$ taken together with the carbon atoms to which they are attached, form a 5- or 6-membered oxygen-containing ring;
$R^4$=absent; provided that when $R^4$ is absent, the dashed line represents a bond;
OH;
$OC(=O)$—Y—$R^{15}$;

OC(=O)—R$^{15}$;
O(C=O)(CH$_2$)$_k$COO(CH$_2$)$_{k'}$;
O(C=O)(CH$_2$)$_k$O(CH$_2$)$_l$COO(CH$_2$)$_k$H; or
ONO$_2$;
R$^5$=H;
R$^{5a}$, R$^{5b}$ taken together are (=O) or
R$^{5a}$, R$^{5b}$ are each independently O(C=O)(CH$_2$)$_k$COO(CH$_2$)$_{k'}$ or
O(C=O)(CH$_2$)$_k$O(CH$_2$)$_l$COO(CH$_2$)$_k$H;
or R$^4$, R$^5$ are connected by —Z—;
R$^6$=H;
CH$_3$;
(C=O)(CH$_2$)$_k$COO(CH$_2$)$_{k'}$;
(C=O)(CH$_2$)$_k$O(CH$_2$)$_l$COO(CH$_2$)$_k$H; or
NO$_2$;
R$^{7a}$=H;
CH$_3$;
CH$_2$(CO)O-alkyl;
CH$_2$(CO)-alkyl;
CH$_2$(CO)-aryl; or
CH$_2$COOCH$_2$CH$_3$; and
R$^{7b}$=H;
CH$_3$;
CH$_2$COOCH$_3$; or
CH$_2$COOCH$_2$CH$_3$; and
or a pharmaceutically acceptable salt thereof.

In certain embodiments,
R$^1$=H;
alkyl (C$_2$-C$_6$);
(C=O)-alkyl or (C=O)-alkenyl, in which alkyl and alkenyl are each a branched or unbranched chain (C$_2$-C$_{22}$); or
(C=O)-alkylidene or (C=O)-alkenylidene, in which alkylidene and alkenylidene are each a branched or unbranched chain (C$_2$-C$_{22}$), attached to an aliphatic or aromatic ring;
R$^3$, and R$^2$ taken together are (=O); or
R$^2$ is OH, and R$^3$ and R$^4$, taken together with the carbon atoms to which they are attached, form a 5- or 6-membered oxygen-containing ring;
R$^4$=OH;
OCH$_3$;
OAcyl (C$_2$-C$_6$); or
ONO$_2$;
R$^{5a}$=OH, O-acyl, O-alkyl, O(CO)—R$^6$; and
R$^{5b}$=H,
or R$^{5a}$=H and R$^{5b}$=OH, O-acyl, O-alkyl, or O(CO)—R$^6$;
R$^6$=H;
CH$_3$;
C(=O)—(C$_2$-C$_6$); or
—(C=O)—O—R$^{5a}$ or R$^{5b}$; and
R$^{7a}$, R$^{7b}$=H, CH$_3$, or CH$_3$, H;
or a pharmaceutically acceptable salt thereof.

In certain embodiments,
R$^1$=H;
alkyl (C$_2$-C$_6$);
(C=O)-alkyl or (C=O)-alkenyl, in which alkyl and alkenyl are each a branched or unbranched chain (C$_2$-C$_{22}$2); or
(C=O)-alkylidene or (C=O)-alkenylidene, in which alkylidene and alkenylidene are each a branched or unbranched chain (C$_2$-C$_{22}$2), attached to an aliphatic or aromatic ring;
R$^3$, R$^2$=O;
R$^4$=H; or
R$^2$ is OH, and R$^3$ and R$^4$, taken together with the carbon atoms to which they are attached, form a 5- or 6-membered oxygen-containing ring;
R$^{5a}$, R$^{5b}$=H, OH or OH, H;
R$^6$=H; and
R$^{7a}$, R$^{7b}$=H, CH$_3$, or CH$_3$, H;
or a pharmaceutically acceptable salt thereof.

In another aspect, the invention provides a method to produce a compound as described hererein, the method comprising the step of oxidizing a descladinosyl macrocyclic compound. In certain embodiments, the step of oxidizing comprises oxidizing using the Swern reaction.

In another aspect, the invention provides a pharmaceutical composition comprising a compound or salt of the invention and a pharmaceutically acceptable carrier.

In another aspect, the invention provides a method of treating an inflammatory disorder, comprising administering to a subject in need thereof an effective amount of a compound or salt of any of claims 1-3.

In another aspect, the invention provides a method of treating an infectious disease, comprising administering to a subject in need thereof an effective amount of a compound or salt of any of claims 1-3.

In another aspect, the invention provides method of treating allergy, comprising administering to a subject in need thereof an effective amount of a compound or salt of any of claims 1-3.

In another aspect, the invention provides a method of treating an immune disorder, comprising administering to a subject in need thereof an effective amount of a compound or salt of any of claims 1-3.

In another aspect, the invention provides a method of manufacturing a pharmaceutical composition for the treatment of an autoimmune disease, comprising mixing a compound or salt of any of claims 1-3 with a suitable pharmaceutically acceptable carrier.

BRIEF DESCRIPTION OF THE DRAWINGS

FIG. 1. Generic structure for the descladinosyl macrolides.

FIG. 2. Compound 2 depicted as the oxidized version and the corresponding hemiketal structure.

FIG. 3. Compound 3, Azithromycin.

FIG. 4. Change in score following induction of collagen induced arthritis in DBA mice treated either with the compound 2, or vehicle (1% citrate).

FIG. 5. Diarrhea severity in mice in which colitis has been induced using DSS and which have subsequently been treated with either Compound 2 or the controls sulfasalazine or its Vehicle Saline or DMSO/1% carboxymethylcellulose or the well known anti-inflammatory kinase inhibitor SB203580.

FIG. 6. Histological severity in mice in which colitis has been induced using DSS and which have subsequently been treated with either Compound 2 or the controls sulfasalazine or its Vehicle Saline or DMSO/1% carboxymethylcellulose or the well known anti-inflammatory kinase inhibitor SB203580.

FIG. 7. Diarrhea severity in mice in which colitis has been induced using TNBS and which have subsequently been treated with either r Compound 2 or the Vehicle (indicated as "TNBS" or Saline instead of TNBS.

FIG. 8. Compound 6.

FIG. 9. Compound 7.

FIG. 10. Weight change in mice in which colitis has been induced using DSS and which have subsequently been treated with either Compound 2, Compound 3, Compound 6 Erythromycin or the controls sulfasalazine or its Vehicle (DSS Only).

FIG. 11. Weight change in mice in which colitis has been induced using DSS and which have subsequently been treated with either Compound 2, Compound 4 the controls sulfasalazine or its Vehicle in comparison with mice in which no disease has been induced.

FIG. 12. Plasma TNFa production in Lewis rats in which liver damage is induced via injection of LPS (4 mg/kg), data are the mean of N=8 and are plotted with the 95% confidence interval.

FIG. 13. TNFa concentration in Bronchoalveolar lavage fluid following aspiration of LPS into the lung. Mice were treated either orally (p.o.) or intranasally (i.n.).

FIG. 14. Examples of Compound 2 Derivatives shown as the oxidized form.

FIG. 15. Effect of compound 2 on hERG currents in hERG expressing cells relative to compound 3.

FIG. 16. Effect of compound 2 or compound 3 on the growth of *E. coli* or *B. pumulius* in liquid medium FIG. 17. Effect of compound 2 on the growth of juvenile mice when given p.o. at 400 μmol/kg.

FIG. 18. Effect of compound 2 or 3 on the normal gut flora of mice when given p.o. at 45 μmol/kg.

FIG. 19. Mass spectrum of COMPOUND 2.

FIG. 20. Fragment mass spectrum of COMPOUND 2 m/z 589.5 adduct mass.

DETAILED DESCRIPTION

Ideally, the goal of retaining anti-inflammatory effects, without selecting for bacterial resistance, would be achieved without adding molecular weight, and most preferably, with reductions in molecular weight as this tends to associate with safety and tolerability.

In the present invention, this concept is elaborated using oxidation products from the erythromycin derived azalide class of macrocycles. Molecular weight is reduced by removing the cladinose group, and molecular weight can be further reduced by modifying the structure of the core macrolide ring. Without wishing to be bound by theory, it is believed that changes to the ring geometry cause the greatest changes in antibiotic activity relative to modification of desosamine.

We have addressed the problem of designing macrocycles for activity on other targets and specifically, the problem of reducing pharmacokinetic and bacterial resistance issues associated with the cladinose sugar such that the resulting compound may be used as an anti-inflammatory compound. Thus, anti-inflammatory activity can be retained while limiting anti-bacterial activity by using oxidized macrolide derivatives.

This invention relates to novel, semi-synthetic macrocycles of the azalide series, particularly to derivatives of Compound 3 and to pharmaceutically acceptable formulations thereof, to a process and intermediates for the preparation thereof, and to their use in the preparation of pharmaceuticals for the treatment of inflammations, neoplasms, cardiovascular diseases, metabolic diseases, gastrointestinal diseases and infections.

The invention comprises descladinosyl macrocycles in which the physical properties are ameliorated by oxidation of the resulting hydroxyl to yield stable keto-hemiketal macrocycles.

The preparation of the compounds described here can be achieved in the following steps:

Removal of the cladinose moiety at position 3 via acid hydrolysis;

Introduction of keto group (with subsequent equilibration to the hemiketal) using selective oxidation;

Deprotection (removal of acyl) of the desosamine OH;

Potential derivatization of the desosamine OH group (a range of options exist in hindered and non-hindered form—see, e.g., the Examples herein);

Desmethylation of the desosamine dimethylamino group and potential derivatization of the free amine;

Potential derivatization of other hydroxyl groups.

It is well known in the chemistry of macrolides that the cladinose sugar is easily hydrolyzed under weakly acidic conditions. It is also known that the 2'-OH is easily and preferentially manipulated despite the presence of other hydroxyl groups in the molecule thereby offering an easy protection scheme.

We found that removal of the cladinose in 2'-acetyl azithromycin results in a molecule that can be directly subjected to a Swern reaction. A Swern reaction is carried out, as is well-known to those skilled in the art, by combining DMSO (generally employed in excess) with oxalyl chloride in an inert solvent like dichloromethane at low temperatures (generally about −60° C.), the alcohol substrate is introduced and after about 10 to 120 minutes, a tertiary amine base added, resulting in formation of the desired aldehyde or in the case of a secondary alcohol, in our case, a ketone. We found that even employing a significant excess of reagent (2 to 5 fold) will not result in over oxidation of the substrate but yield the desired ketone in good yield. The same compound, after removal of the protective acetyl group, has been described earlier; see U.S. Pat. No. 6,369,035, using a similar method of oxidation. The resulting compound can be further modified, for example by esterification at 2'-OH after removal of the acetyl group at this position, or by forming a carbonate at C-12/C13.

It will be appreciated that other oxidation conditions (such as e.g., Dess-Martin periodinane) may also be useful for oxidation of the secondary alcohol to the ketone.

The compounds prepared by this method have a number of important characteristics relative to the parent macrocycles:

They exhibit low mammalian toxicity

They interact less with the human ether-a-go-go protein (hERG)

Have limited anti-microbial activity

They are anti-inflammatory

They may be formulated for delayed release and thus used for lower intestine inflammation.

This type of chemical approach can be performed on a variety of macrocycles including those derived from erythromycin. In certain embodiments, the macrocycle is derived from the azalide series. In certain further embodiments, the macrocycle is prepared as one or more acyl or similar esters and specifically as an ester to the desosamine hydroxyl that is known to coordinate with the ribosome target.

In certain embodiments, the macrolides with anti-inflammatory properties and no anti-bacterial effect have a molecular weight (MW) lower than 748 mass units. In certain embodiments, the MW is less than 694 mass units. In certain embodiments, the MW is less than 674 mass units, and in certain embodiments, the MW is less than 646 mass units. In certain embodiments, the MW is less than 620 mass units, or the MW is less than 590 mass units, or the MW is less than 574 mass units. In still further embodiments, the MW is less than 548 mass units.

In addition to removing cladinose, reactions that maintain or increase the lack of antibacterial effect include forming N-oxides on the amines, demethylating the amines, introduction of a double bond in the macrolactone ring, or forming ethers between macrolactone hydroxyl groups. Thus, in certain embodiments, the invention relates to compounds having N-oxides on one or more amines. In certain embodiments, the invention relates to compounds having a double bond in the macrolactone ring. In certain embodiments, the invention relates to compounds having ethers between macrolactone hydroxyl groups (e.g., formation of hemiketals).

In another aspect, this invention features a method for treating an autoimmune, inflammatory, viral, cardio-vascular, metabolic or immune disorder. The method includes administering to a subject in need thereof an effective amount of a compound described herein. In certain embodiments, the compound is administered to a subject (e.g., a mammal, e.g., a human, cat, dog, cow, horse, mouse, rat, monkey, or the like) in an amount ranging from about 0.1 mg/day to about 10 g/day, or between 1 mg and 5 g/day, or between 10 mg and 1 g per day.

Optionally, the method includes co-usage with other anti-inflammatory agents or therapeutic agents. The use of the compounds described herein exerts a positive effect in part because of the preferential access of the compounds to immune cells including neutrophils, monocytes, eosinophils, macrophage, alveolar macrophage, B and T-lymphocytes, NK cells, giant cells, Kupfer cells, glial cells, and similar target cells.

In a preferred embodiment, the disease to be treated is an inflammatory disease, an autoimmune disease, a process of graft rejection, a cancer associated with inflammation or a disease associated with an excess immune reaction such as arthritis, inflammatory bowel disease (ulcerative colitis or Crohn's disease), multiple sclerosis, allergy, reaction to infection or sepsis.

To treat the disease, the macrocycle is administered to a patient in need at a dose of between 0.1 and 100 μmol/kg via a suitable route and formulation. Administration of the compound is continued for as long as necessary. Under some circumstances, the initial dose will be higher than the subsequent doses.

Formulating the macrocycle in a pharmaceutically acceptable dosage form provides for a method of treating the patient such that signs of excess immune system activity are reduced. In a preferred embodiment, the macrocycle is formulated for oral administration. In another embodiment, the macrocycle is formulated with enteric protection to provide for release in the lower abdominal tract. Another embodiment, the macrocycle is formulated for delayed release or slow release in addition to enteric coating.

In a preferred embodiment, the macrocycle is one in which cladinose is removed, and in a still further preferred embodiment, one in which the point of attachment is further oxidized as in FIG. 2. In a still preferred embodiment, the 2-OH of the point of attachment of cladinose is free.

The non-antibacterial macrolides can influence cytokine production in response to LPS stimulus. Examination of in vitro results presented in Example 31 suggests that the compounds are able to influence production of TNFa, GMCSF and IL-12 in response to stimulation with lipolysaccharide (LPS). Thus, in certain embodiments, administration of the compounds to a subject can provide one or more of: reduction in TNFa production, reduction of IL-12 production and increase of GMCSF production in response to LPS in the presence of a concentration of 50 μM of the compounds.

In certain embodiments, the compound is a macrolide that has an $IC_{50}$ for *Staphylococcus aureus* in vitro of more than 700 μM, and in certain embodiments, the compound has the ability to modify cytokine expression when incubated with J774 cells, and in certain embodiments, the compound has a MW of less than 748 AMU. In certain embodiments, the compound has a MW of less than 674 and, in certain embodiments, the compound suppresses production of IL-12 by more than 30% relative to vehicle treated cells when incubated with J774 cells according to the method described in Example 31 herein.

In certain embodiments, the compound has a MW of less than 734, or less than 633.

In certain embodiments, the compound inhibits TNF production in J774 cells by 20% at 50 μM. In certain embodiments, the compound is not cytotoxic at 50 μM to J774 cells as evaluated by alamar blue staining.

DEFINITIONS

The term "cyclic" refers to a hydrocarbon cyclic ring including fully saturated, partially saturated, and unsaturated mono-, bi, and tri-cyclic rings having 4 to 34 ring atoms, preferably, 7 to 10, or 10 to 15 ring atoms. The term "heterocyclic" refers to a hydrocarbon cyclic ring including fully saturated, partially saturated, and unsaturated mono-, bi, and tri-cyclic rings having 4 to 34 ring atoms, preferably, 7 to 10, or 10 to 15 ring atoms having one or more heteroatoms, such as S, O, or N in each ring.

The term "sugar" refers to a mono-, di-, or tri-saccharide including deoxy-, thio-, and amino-saccharides. Examples of sugar include, but are not limited to, furanose and pyranose.

The terms "halogen" and "halo" refer to radicals of fluorine, chlorine, bromine or iodine. The term "macrolactone" or "macrocycle" refers to a large lactone ring (i.e., cyclic ester) having at least 10 ring atoms. The term "macrolide" refers to a chemical compound characterized by a large lactone ring (having at least 10 ring atoms) containing one or more keto and hydroxyl groups, or to any of a large group of antibacterial antibiotics containing a large lactone ring linked glycosidically to one or more sugars; they are produced by certain species of *Streptomyces* and inhibit protein synthesis by binding to the 50S subunits of 70S ribosomes. Examples include erythromycin, azithromycin (compound 3), and clarithromycin. The term "ketolide" refers to a chemical compound characterized by a large lactone ring (having at least 10 ring atoms) containing one or more keto groups.

The term "alkyl" (or "alkenyl" or "alkynyl") refers to a hydrocarbon chain that may be a straight chain or branched chain, containing the indicated number of carbon atoms. For example, $C_1$-$C_{10}$ indicates that the group may have from 1 to 10 (inclusive) carbon atoms in it. Alkenyl groups and alkynyl groups have one or more double or triple carbon-carbon bonds, respectively, in the chain. Unless otherwise stated, an alkyl group has from 1 to 10 carbon atoms, or from 1 to 6 carbon atoms. Similarly, unless otherwise stated, an alkenyl group or alkynyl group has from 2 to 10 carbon atoms, or from 2 to 6 carbon atoms. In certain embodiments, an alkyl group is a methyl, ethyl, propyl, or isopropyl group.

The term "aryl" refers to a hydrocarbon ring system (monocyclic or bicyclic) having the indicated number of carbon atoms and at least one aromatic ring. Examples of aryl moieties include, but are not limited to, phenyl, naphthyl, and pyrenyl.

The term "heteroaryl" refers to a ring system (monocyclic or bicyclic) having the indicated number of ring atoms including carbon atoms and at least one aromatic ring. The ring system includes at least one heteroatom such as O, N, or S (e.g., between 1 and 4 heteroatoms, inclusive, per ring) as part of the ring system. Examples of heteroaryl moieties include, but are not limited to, pyridyl, furyl or furanyl, imidazolyl, benzimidazolyl, pyrimidinyl, thiophenyl or thienyl, quinolinyl, indolyl, and thiazolyl.

The term "alkoxy" refers to an —O-alkyl radical.

The term "cycloalkyl" refers to a non-aromatic hydrocarbon ring system (monocyclic or bicyclic), containing the indicated number of carbon atoms.

The term "heterocycloalkyl" refers to a non-aromatic ring system (monocyclic or bicyclic), containing the indicated number of ring atoms including carbon atoms and at least one heteroatom such as O, N, or S (e.g., between 1 and 4 heteroatoms, inclusive, per ring) as part of the ring system.

The compounds described herein have a range of utilities including use as anti-inflammatory compounds, inhibitors of neuro degeneration, anti-viral compounds, modulators of ion-channels, cardio-vascular modulators, metabolic modulators and immune modulators. In many instances, their utility is related to the effects on cells of the macrophage type either as phagocytes or antigen presenting cells. Such an example is seen in cardiovascular diseases such as atherosclerosis where there is a strong inflammatory component to the events that result in the thickening and fragmentation of the plaque. This inflammation may be effectively reduced by the application of a range of agents that interact with the macrophage class.

Reference to atoms like hydrogen or carbon also includes their isotopes deuterium and Carbon 13.

The compounds described herein (e.g., in Examples 1-10, 21-29) include the compounds themselves, as well as their salts, if applicable. Such salts, for example, can be formed between a positively charged substituent (e.g., amino) on a compound and an anion. Suitable anions include, but are not limited to, chloride, bromide, iodide, sulfate, nitrate, phosphate, citrate, methanesulfonate, trifluoroacetate, formate and acetate. Likewise, a negatively charged substituent (e.g., carboxylate) on a compound can form a salt with a cation. Suitable cations include, but are not limited to, sodium ion, potassium ion, magnesium ion, calcium ion, and an ammonium cation such as tetramethylammonium ion.

In addition, some of the compounds of this invention have one or more double bonds, or one or more asymmetric centers. Such compounds can occur as racemates, racemic mixtures, single enantiomers, individual diastereomers, diastereomeric mixtures, and cis- or trans- or E- or Z-double isomeric forms.

Furthermore, the aforementioned compounds also include their N-oxides. The term "N-oxides" refers to one or more nitrogen atoms, when present in a compound, are in N-oxide form, i.e., N→O.

Combinations of substituents and variables envisioned by this invention are only those that result in the formation of stable compounds. The term "stable", as used herein, refers to compounds which possess stability sufficient to allow manufacture and which maintains the integrity of the compound for a sufficient period of time to be useful for the purposes detailed herein (e.g., treating a disease).

In a further preferred embodiment, the resulting compound is formulated as a salt with an organic counter ion including formates, acetates, propionates and citrates.

The present invention also features a pharmaceutical composition including at least one compound of this invention and a pharmaceutically acceptable carrier. Optionally, the pharmaceutical composition includes one or more other therapeutic agents.

This invention further features a method for making any of the compounds described above. The method includes taking any intermediate compound delineated herein, reacting it with any one or more reagents to form a compound of this invention including any processes specifically delineated herein.

Also within the scope of this invention are compositions having one or more of the compounds of this invention for use in treating various diseases described above, and the use of such a composition for the manufacture of medication for the just-described use.

Other advantages, objects, and features of the invention will be apparent from the description and drawings, and from the claims.

To practice the method of treating a disease, the compounds of this invention can be administered to a patient, for example, in order to treat a disease described above. The compound can, for example, be administered in a pharmaceutically acceptable carrier such as physiological saline, in combination with other therapeutic agents, and/or together with appropriate excipients. The compound described herein can, for example, be administered by injection, intravenously, intra-arterially, subdermally, intraperitoneally, intramuscularly, or subcutaneously; or orally, buccally, nasally, transmucosally, topically, in an ophthalmic preparation, by inhalation, by intracranial injection or infusion techniques, with a dosage ranging from about 0.1 to about 20 mg/kg of body weight, preferably dosages between 10 mg and 1000 mg/dose, every 4 to 120 hours, or according to the requirements of the particular therapeutic agent. The methods herein contemplate administration of an effective amount of compound or compound composition to achieve the desired or stated effect. Lower or higher doses than those recited above may be required. Specific dosage and treatment regimens for any particular patient will depend upon a variety of factors, including the activity of the specific compound employed, the age, body weight, general health status, sex, diet, time of administration, rate of excretion, therapeutic agent combination, the severity and course of the disease, condition or symptoms, the patient's disposition to the disease, condition or symptoms, and the judgment of the treating physician.

Pharmaceutical compositions of this invention comprise a compound of this invention or a pharmaceutically acceptable salt thereof; and any pharmaceutically acceptable carrier, adjuvant or vehicle. Such compositions may optionally comprise additional therapeutic agents. The compositions delineated herein include the compounds of the formulae delineated herein, as well as additional therapeutic agents if present, in amounts effective for achieving a modulation of a disease.

The term "pharmaceutically acceptable carrier or adjuvant" refers to a carrier or adjuvant that may be administered to a patient, together with a compound of this invention, and which does not destroy the pharmacological activity thereof and is nontoxic when administered in doses sufficient to deliver a therapeutic amount of the compound.

Pharmaceutically acceptable carriers, adjuvants and vehicles that may be used in the pharmaceutical compositions of this invention include, but are not limited to, ion exchangers, alumina, aluminum stearate, lecithin, self-emulsifying therapeutic agent delivery systems (SEDDS) such as D-alpha-tocopherol polyethylene glycol 1000 succinate, surfactants used in pharmaceutical dosage forms such as Tweens or other similar polymeric delivery matrices, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethyl cellulose, polyacrylates, waxes, polyethylene-polyoxypropylene-block polymers, polyethylene glycol and wool fat. Cyclodextrins such as I-, θ-, and K-cyclodextrin, or chemically modified derivatives such as hydroxyalkyl cyclodextrins, including 2- and 3-hydroxypropyl-θ-cyclodextrins, or other solubilized derivatives may also be advantageously used to enhance delivery of compounds of the formulae described herein. Oil solutions or suspensions may also contain a long-chain alcohol diluent or dispersant, or carboxymethyl cellulose or similar dispersing agents which are commonly used in the formulation of pharmaceutically acceptable dosage forms such as emulsions and or suspensions.

The pharmaceutical compositions of this invention may be orally administered in any orally acceptable dosage form including, but not limited to, capsules, tablets, emulsions and aqueous suspensions, dispersions and solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions and/or emulsions are administered orally, the active ingredient may be suspended or dissolved in an oily phase is combined with emulsifying and/or suspending agents. If desired, certain sweetening and/or flavoring and/or coloring agents may be added.

The pharmaceutical compositions of this invention may also be administered in the form of suppositories for rectal administration. These compositions can be prepared by mixing a compound of this invention with a suitable non-irritating excipient which is solid at room temperature but liquid at the rectal temperature and therefore will melt in the rectum to release the active components. Such materials include, but are not limited to, cocoa butter, beeswax and polyethylene glycols.

Topical administration of the pharmaceutical compositions of this invention is especially useful when the desired treatment involves areas or organs readily accessible by topical application. For application topically to the skin, the pharmaceutical composition should be formulated with a suitable ointment containing the active components suspended or dissolved in a carrier. Carriers for topical administration of the compounds of this invention include, but are not limited to, mineral oil, liquid petroleum, white petroleum, propylene glycol, polyoxyethylene polyoxypropylene compound, emulsifying wax and water. Alternatively, the pharmaceutical composition can be formulated with a suitable lotion or cream containing the active compound suspended or dissolved in a carrier with suitable emulsifying agents. Suitable carriers include, but are not limited to, mineral oil, sorbitan monostearate, polysorbate 60, cetyl esters wax, cetearyl alcohol, 2-octyldodecanol, benzyl alcohol and water. The pharmaceutical compositions of this invention may also be topically applied to the lower intestinal tract by rectal suppository formulation or in a suitable enema formulation. Topically-transdermal patches are also included in this invention.

The pharmaceutical compositions of this invention may be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art.

A suitable in vitro assay can be used to preliminarily evaluate a compound of this invention in treating a disease. In vivo screening can also be performed by following procedures well known in the art. See, e.g., the specific examples below.

ADDITIONAL REFERENCES

Axton et al., 1992, J. Chem. Soc. Perkin Trans. 12203 ff.
Bartlett et al., 1991, Agents and Actions, 32 10-21.
Benslay D N and Bendele A M, 1991, Agents Actions 34: 254.
Billingham et al., 1954. Proc. R. Soc. 143: 43-55.
Bright et al. J. Antibiotics, 41 (1988), 1029
Hutchins R O, Hoke D, Keogh J, Koharstki D, 1969, Sodium Borohydride in Dimethyl Sulfoxide or Sulfolane. Convenient Systems for Selective Redutions of Primary, Secondary, and Certain Tertiary Halides and Tosylates. Tetrahedron Letters, 3495-3498.
Ianaro et al., 2000, Anti-inflammatory activity of Macrolide Antibiotics. J. Pharmacol. Ex. Therapeutics. 292:156-161.
Labro M T and Abdelghaffar H, 2001, Immunomodulation by macrolide antibiotics. J. Chemother. February; 13(1):3-8. Review.
Labro M T, 1998, Anti-inflammatory activity of macrolides: a new therapeutic potential? J. Antimicrobial Chemother. 41, Suppl., 37-46.
H. Laufen et al., Drug Res. 40 (1990), 686.
Mencarelli A, et al., Development of non-antibiotic macrolide that corrects inflammation-driven immune dysfunction in models of inflammatory bowel diseases and arthritis. Eur J. Pharmacol. 2011 Aug. 31; 665(1-3):29-39.
R. P. Rapp, Ann. Pharmacotherap. 32 (1998), 785; b)
Quallich L G, Greenson J, Haftel H M, Fontana R J, 2001, Is it Crohn's disease? A severe systemic granulomatous reaction to sulfasalazine in patient with rheumatoid arthritis, BMC Gastroenterol; 1(1):8.
W. Schönfeld, S. Mutak, in: M. Parnham, J. Bruinvels, W. Schönfeld, H. Kirst (Eds.), Macrolide Antibiotics, Birkhauser, Basel 2002, p. 101 4) lit. cit. 3), p. 87
Schroit A J, Madsen J, Nayar R, 1986, Liposome-cell interactions: in vitro discrimination of uptake mechanism and in vivo targeting strategies to mononuclear phagocytes., Chem Phys Lipids. Jun.-Jul.; 40(2-4):373-93.

PATENTS AND PENDING PATENT APPLICATIONS

| | | |
|---|---|---|
| PCT03/070173 | February 2002 | Burnet et al |
| U.S. Pat. No. 4,328,334 | May 1982 | Kobrehel et al. |
| U.S. Pat. No. 3,478,014 | November 1969 | Djokic et al. |
| U.S. Pat. No. 3,652,537 | March 1972 | Massey |
| U.S. Pat. No. 4,988,677 | January 1991 | Franco |
| U.S. Pat. No. 5,543,400 | August 1996 | Agouridas |
| US2001/0053782 | December 2000 | Blumenkopf et al. |
| PCT03/070254A1 | February 2002 | Burnet et al. |
| WO2004029067 | February 2003 | Berdik et al. |
| WO09/963937 | July 1999 | Griffin |
| EP0283055 | September 1988 | Carevic and Djokic |
| EP0627406A1 | October 1992 | Fujita et al. |

All references cited herein, whether in print, electronic, computer readable storage media or other form, are expressly incorporated by reference in their entirety, including but not limited to, abstracts, articles, journals, publications, texts, treatises, internet web sites, databases, patents, and patent publications.

The invention will be further described in the following examples. It should be understood that these examples are for illustrative purposes only and are not to be construed as limiting this invention in any manner.

EXAMPLES

Unless otherwise specified, all commercially available reagents and solvents were used without further purification. All Chemical names and structures were generated from ChemDraw Ultra (Cambridge Soft).

Example 1

Compound 1

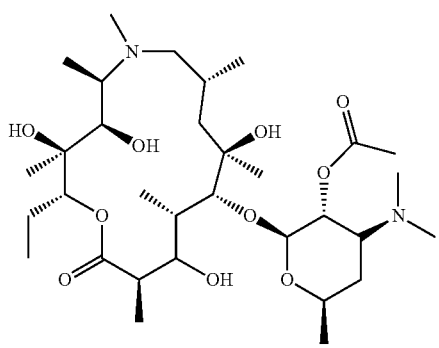

15.8 g (21.1 mmol) Compound 3 (9a-aza-9a-methyl-9-deoxo-9a-homoerythromycin A, Azithromycin) was dissolved in an ice-cold 6 N aqueous hydrogen chloride solution (100 ml). The reaction mixture was stirred at 0° C. for 4 hours. The solution turned from yellow to green. The solution was poured on ice (200 g) and 28 ml sodium hydroxide solution (50%) was added. The solution was extracted with ethyl acetate (300 ml). The organic layer was discarded. After addition of 30 ml sodium hydroxide solution (50%) to the water layer a colorless precipitate formed. The suspension was extracted with dichloromethane (300 ml). The organic layer was separated, dried over $Na_2SO_4$ and concentrated under reduced pressure. After drying in high vacuum 12.8 g (100%) of colorless foam were obtained which were used without further purification.

The product was dissolved in dry dichloromethane (150 ml) and 3.1 ml (32.7 mmol) acetic acid anhydride was added. The solution was stirred at room temperature overnight, then diluted with dichloromethane (200 ml) and washed with saturated sodium bicarbonate solution (150 ml). The organic layer was separated, dried over $Na_2SO_4$ and concentrated under reduced pressure. 12.3 g (92%) of Compound 1 were obtained as colorless foam, which was dried in high vacuum and used without further purification.

Example 2

Compound 2

Chemical name: 11-(4-Dimethylamino-3-hydroxy-6-methyl-tetrahydro-pyran-2-yloxy)-2-ethyl-3,4,10-trihydroxy-3,5,6,8,10,12,14-heptamethyl-1-oxa-6-aza-cyclopentadecane-13,15-dione; $C_{30}H_{56}N_2O_9$, MW: 588.78, exact Mass: 588.40

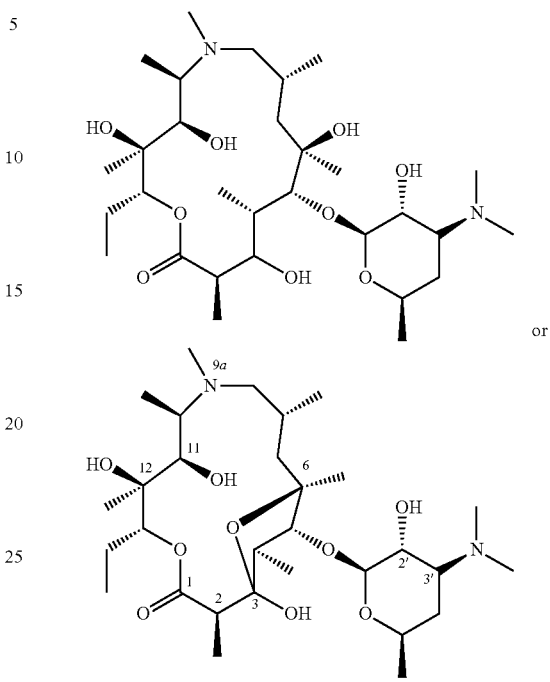

A solution of 610 mg (4.5 mmol) N-chlorosuccinimide in dry dichloromethane (50 ml) was chilled to −30° C. and 590 µl (8 mmol) dimethylsulfide were added. A colorless precipitate formed immediately and the suspension was kept between −30° C. and −10° C. for 30 min. Then the reaction mixture was cooled to −40° C. and 1.9 g (3.0 mmol) of compound 1 were added in one portion. After 20 min, the precipitate was completely dissolved and 770 µl (4.5 mmol) of ethyl diisopropylamine were added to the colorless solution. The reaction mixture was allowed to slowly reach ambient temperature. Stirring was continued at room temperature for another hour. The reaction mixture was diluted with dichloromethane (50 ml) and washed with saturated sodium bicarbonate solution (100 ml). The organic layer was separated, dried over $Na_2SO_4$ and concentrated under reduced pressure. Colorless oil was obtained which was re-dissolved in methanol (75 ml) and stirred at 50° C. overnight. The solvent was removed under reduced pressure and the residue subjected to column chromatography on silica gel with chloroform/methanol/7N ammonia in methanol (C:M:A 20:1:1) as eluent to yield 1.0 g (59%) of Compound 2 as colorless oil.

Example 3

Analysis and Detection of Compound 2

The compound is easily ionized in ESI-MS and can be detected in picomolar concentration routinely. Quantification by HPLC-MS (ESI-Ion Trap) is possible down to 50 µl of a 10 nM solution (ca. 30 pg). The compound appears as monocharged ion with m/z=589.5 and as double protonated ion with m/z=295. Fragmentation of the peak at m/z=589.5 leads to a fragment spectrum with significant peaks at m/z=571 (M−$H_2O$) and m/z=396 (M−$H_2O$-desosamine), the latter one indicative in MRM experiments and also characteristic for conjugates of Compound 2. See FIG. 19.

Example 4

¹H and ¹³C NMR Spectra of Compound 2

¹H NMR spectrum (assignment as far as possible):

| δ (ppm) | multiplicity | assignment |
|---|---|---|
| 4.94 | d | 13-H |
| 4.20 | d | 1'-H |
| 3.74 | d | 5-H?, 11-H? |
| 3.68 | br. s | OH? |
| 3.51 | ddq | 5'-H |
| 3.30 | s | 11-H?, 5-H? |
| 3.23 | dd | 2'-H |
| 2.59 | q | 2-H |
| 2.49 | ddd | 3'-H |
| 2.28 | s | $(NMe)_2$—H |
| 2.04 | m | |
| 1.93 | br. s | |
| 1.76 | br. s | |
| 1.68 | ddd | 4'-H |
| 1.38 | s | |
| 1.2-1.6 | m | |
| 1.16 | br. s | |
| 1.10 | m | |
| 1.04 | d | |
| 0.92 | t | |

¹³C NMR spectrum (assigned as far as possible):

| δ (ppm) | assignment |
|---|---|
| 176.6 | 1 |
| 106.6 | 1' |
| 102.7 | 3 |
| 95.3 | C-5?/C-11? |
| 82.9 | 6 |
| 74.0 | 12 |
| 70.1 | 2' |
| 69.8 | 5' |
| 66.9 | 9 |
| 65.8 | 3' |
| 62.2 | 10? |
| 49.8 | 2/4 |
| 49.0 | 2/4 |
| 41.9 | 7 |
| 40.6 | N—Me |
| 31.4 | |
| 28.7 | 4' |
| 26.9 | |
| 22.2 | |
| 21.4 | |
| 14.1 | |
| 13.1 | |
| 11.9 | |

The assignments were made by using GHSQC and GHMQC spectra and a published Compound 3 spectrum for comparison. Not all carbons could be detected, and assignments in the lower ppm area were not possible. The absence of a carbonyl signal above 200 ppm with concomitant appearance of a signal at 102 ppm which can be assigned to C-3, and significant shifts of the carbon atoms 5 and 6 highly indicate an acetal formation between the positions 3 and 6.

Example 5

High-Performance Liquid Chromatography of Compound 2 and its Isomers and Impurities Compound 2 can be analyzed by HPLC under the following conditions:
For analysis in biological tests, a Prontosil-C18-ace-EPS column (50×3 mm, 5 µM material, Bischoff) was used, with a gradient starting with 20% B, increasing to 24% B after 30 s, to 38% B after 45 s, to 43% B after 3 min. Compound 2 elutes after 1.5 to 2 min at a flow rate of 4000/min. (A=0.05% HCOOH in Water, B=0.05% HCOOH in acetonitrile.). Standard injection volume is 50 µl.

For the separation of isomers of Compound 2 the following method is suitable: An OCS AQ column (250×10 mm, 10 µM material, YMC), gradient from 16 to 18.5% B within 7 min (A, B: see above) at 4 ml/min.

For the separation of various side products, the following procedure is suitable: A Prontosil C18-H column (50×4.6 mm, 0.3 µM material, Bischoff), 0-1 min 5% B, 1.01 min 10% B, 7 min 18% B, 8.5 min 35% B, 8.51 min 100% B. (A, B: see above). Flow rate 800 µl/min.

Example 6

Scale-Up Procedures for Bulk Preparation of Compound 2 Up to 200 g—Scale

The following oxidative conditions may be used as alternative methods:
Dimethylsulfide/NCS
PCC
Dess-Martin Periodinate
DMSO/DCC
DMSO/DCC/TFA
$DMSO/Ac_2O$
DMSO/Acetyl chloride
DMSO/TFAA
$SO_3$-Pyridine/DMSO
Thioanisole/NCS
NaOCl/TEMPO Based on our experience, however, the Swern oxidation proved to be the superior method in terms of yields, purity and ease of workup.

Example 7

Compound 4

Chemical Name: 14-(4-Dimethylamino-3-hydroxy-6-methyl-tetrahydro-pyran-2-yloxy)-5-ethyl-1,6-dihydroxy-2,6,8,9,11,13,15-heptamethyl-4,16-dioxa-9-aza-bicyclo[11.2.1]hexadecane-3,7-dione (Generated by ChemDraw) $C_{30}H_{54}N_2O_9$, MW: 586.76, exact mass: 586.38

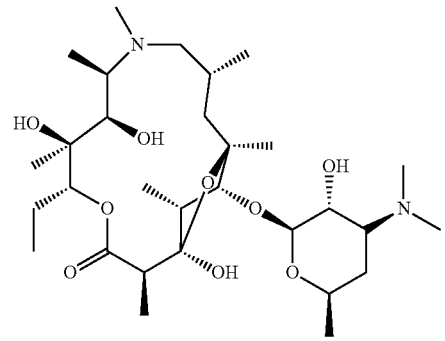

Compound 4 is the over oxidation product in the synthesis of Compound 2. It is best achieved via the Corey-Kim reaction: 165 mg of 2'-unprotected Compound 1 were dissolved in 4 ml of dry dichloromethane and added dropwise at −30° C. to a pre-formed mixture of 120 µl of dimethylsulfide and 180 mg N-bromosuccinimide. The reaction is stirred for 30 min at −10° C., followed by the addition of 3000 ethyldiisopropylamine. The precipitate that initially formed, dissolved upon stiffing at 0° C. for 30 min. At this point, all volatiles were removed by vacuum evaporation and the resulting residue stirred with 25 ml of methanol for 1 h under reflux. The methanol was removed by evaporation. Chromatography of the residue with ammonia saturated ethyl acetate and subsequently with C:M:A (300:15:15) yields 92.6 mg (61%) of the colorless product.

Compound 4 is a colorless solid. The impurity profile is similar to that of Compound 2, but a compound with m/z=647.5 are in much higher concentration than the other compounds. The ease of hydrolysis of the intermediate acetate of Compound 4 leads to the assumption, that 2'-esters of Compound 4 are significantly more labile than those of Compound 2. Compound 4 forms an [M+H]$^+$ ion at m/z=587.4 and an [M+2H]$^{2+}$ ion at m/z=294.3. The former fragments to a compound with m/z=394.2, the latter to m/z=430.2, 158.1, and 394.2 as minor signal. TLC: C:M:A (20:1:1) as eluting solvent, Compound 4 has an $R_f$ value of 0.65.

Example 8

Compound 5a and Compound 5b

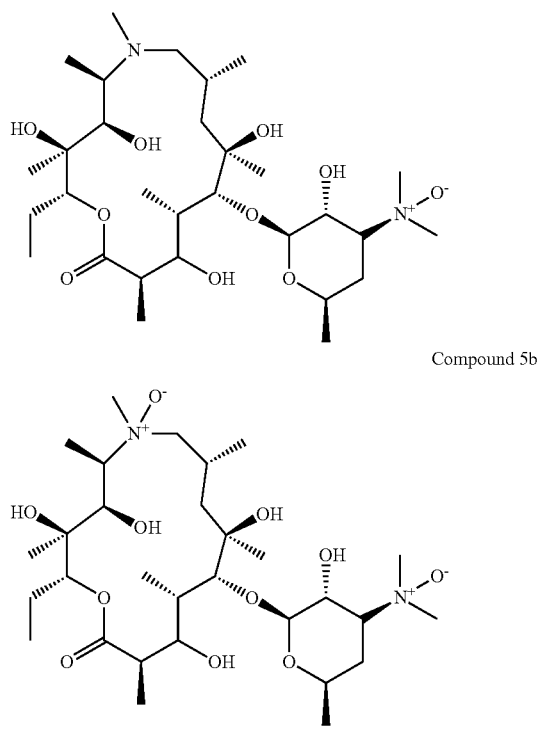

589 mg of Compound 2 was dissolved in methanol (30 ml), and to this was added, 1.25 ml of hydrogen peroxide solution (60% w/v). The mixture was stirred overnight and additional 120 µl of the hydrogen peroxide solution was added. Reaction progress was monitored by TLC (Chloroform:MeOH:NH$_3$ in MeOH (7N)/12.5:2:0.5) for the disappearance of the starting material. Sodium bisulfite (2.8 g) was dissolved in H2O (20 ml) and the solution added to the reaction mixture. The solvents were removed in vacuo and the residue taken up in ethyl acetate/methanol mixture (12:1). The cloudy solution was filtered thru celite and the solvent reamoved in vacuo to get a white foam (209 mg), which was purified by Column chromatography (C:M: A/15:4:1) to get compound 5a (56 mg; 10% yield) and compound 5b (26 mg; 4% yield). A better route to achieving compound 5a in better yields is delineated below.

An alternative route to the Compound 5a: 589 mg of Compound 2 was taken up in dichloromethane (3 mL). To the stirred reaction solution was added at 0° C., 208 mg meta-chloroperbenzoic acid. Reaction progress was monitored by TLC(C:M:A (12.5:2:0.5) until the disappearance of the starting material is observed (Reaction was allowed to proceed for 72 h with no significant progress after 48 h). The solvent was removed in vacuo to obtain a yellowish residue which was subjected to Column Chromatography (C:M:A/15:4:1) produced the desire product, Compound 5a (450 mg; 75% yield) as a white foam.

Example 9

Compound 5

Chemical Name: [14-(4-Dimethylamino-3-hydroxy-6-methyl-tetrahydro-pyran-2-yloxy)-5-ethyl-1,6,7-trihydroxy-2,6,8,9,11,13,15-heptamethyl-3-oxo-4,16-dioxa-9-aza-bicyclo[11.2.1]hexadec-2-yl]-acetic acid ethyl ester (generated by Chemdraw): $C_{34}H_{62}N_2O_{11}$, MW: 674.86, exact mass: 674.44.

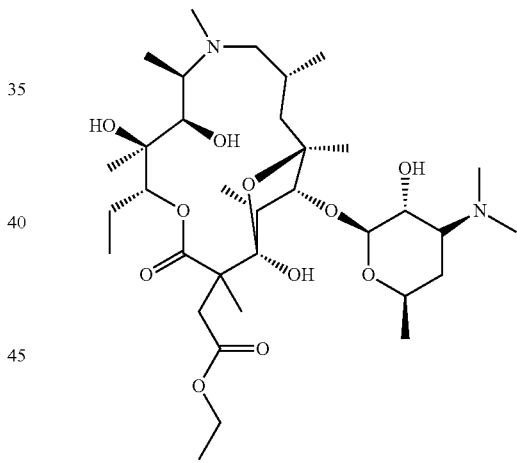

88 mg of Compound 5a were dissolved in 8 ml of dry N,N-dimethyl acetamide. 37 mg of potassium tert-butylate was added. The resulting yellow solution was cooled to −75° C., and 50 µl of ethyl bromoacetate. After 10 minutes, 100 µl of triethylamine were added. The mixture was stirred for an additional hour, at which point, 100 µl acetic acid, 5.5 mg palladium (10% on charcoal) and 10 ml of ethanol were added. The reaction was kept in an atmosphere of hydrogen for 3 h.

Extractive workup with water/ethyl acetate yielded a residue, that was subjected to chromatography over silica gel with C:M:A (15:1:1). The yield was approximately 35 mg of a yellowish sticky oil.

Compound 5 displays an [M+H]$^+$ ion at m/z=675.3. Fragmentation signals: 657.3, 482.2, 399.2, and 396.2. TLC C:M:A (30:2:1): $R_f$ value of 0.59.

Example 10

Ester Formation of Compound 2

To a solution of 1.2 g of Compound 2 and 550 mg of tetra-decanoic acid in 12 ml of dichloromethane was added, at ambient temperature, 500 mg of DCC in one portion. After stiffing for another 3 h the mixture was filtered, diluted with 30 ml of ethyl acetate and extracted with citric acid (10% in water, 3×60 ml). The combined aqueous extracts were cooled in an ice bath and adjusted with potassium carbonate to pH 10 and the mixture was extracted with ethyl acetate (3×20 ml). After drying ($Na_2SO_4$) the organic phase were concentrated in vacuum to yield a white solid. Further purification can be achieved by chromatography on silica gel, elution with chloroform/isopropanol/ammonia (7M in methanol) 50:1:1.

Example 11

Uptake of Compound 2

Buffy coat preparations were used for the determination of immune cell uptake of the compound. Buffy coat was obtained from donor blood by simple centrifugation of whole blood (4795 g for 10 minutes). Following centrifugation, plasma was collected from the surface, after which immune cells were expressed from the donor bags along with the erythrocytes lying immediately below the leukocyte layer. 5 ml of the resulting cell suspension were dispensed into T25 culture flasks. Compounds were added to a final concentration between 1 and 10 µM and the suspensions incubated at 37° C., in a 5% $CO_2$ atmosphere. For analysis of uptake kinetics, samples were withdrawn at 0, 2, 5, 10, 30, 60, 90, 180, or 240 min after substrate addition. For screening purposes, samples were taken at 0 and 90 minutes. (PBS 73 mM NaCl, 2.7 mM KCl, 1.5 mM $KH_2PO_4$, 8 mM $Na_2HPO_4$, pH 7.4; DPBS 137 mM NaCl, 3 mM KCl, 8 mM $Na_2HPO_4$, 1 mM $KH_2PO_4$, 1 mM $CaCl_2$, 0.5 mM $MgCl_2$, 5 mM Glucose, pH 7.4). Cell fractions were prepared using density gradient centrifugation. Mononuclear cells and polymorphonuclear cells were separated from erythrocytes essentially by layering the cell suspension on a viscous medium typically composed of a solution containing Ficoll or similar (commercial suppliers include: Lymphoprep, Axis Shield, 1031966; Lymphoflot HLA, 824010; or PMN Separation Medium Robbins Scientific 1068-00-0). The layered suspension was then centrifuged at 600 g, 20 min, after which the cell fractions and the plasma (incubation medium) fraction were removed by gentle aspiration, washed twice in PBS buffer, followed by estimation of the cell number and pellet volume. Cell preparations were lysed in water and the debris sedimented at 16100 g, 10 min. The supernatant was recovered and subsampled for protein and DNA content. Protein in the supernatant was precipitated by bringing the solution to 100% v/v ethanol and centrifuging again at 16100 g for 10 min. Compound uptake was normalized according to cytoplasmic volume of cells in order to obtain the average concentration in the cells. Cell volume was estimated by correlation of DNA, protein or haem content of lysed cell aliquots to cell number and packed volume prior to lysis. Cell lysates were analysed using a HP 1100 HPLC System (Agilent Technologies, Waldbronn, Germany) with a Kromasil 3.5µ C18, 50×2.0 mm column and guard cartridge system (both, Phenomenex, Aschaffenburg, Germany) run at 30° C. A gradient elution was performed using water, 0.0 5% formic acid (A) and acetonitrile 0.05% formic acid (B) (0 min. 5% B, 2.5 min 5% B, 2.8 min 40% B, 10.5 min 85% B, 12.0 min 95% B, 16.5 min 95% B) at a flow rate of 300 µl/min. Re-equilibration of column was at 5% B, at a flow rate of 750 µl/min for 2.4 min. The HPLC-eluate from retention time 0.0 min to 2.5 min was directed directly to waste. Detection was via a UV cell at 214 nm followed by a ⅙ split to an An API-qTOF 1 (Micromass, Manchester, UK) mass spectrometer, (calibrated daily using a mixture of NaI, RbI and CsI). The mass spectrometer was routinely operated in the positive electro-spray ionization mode using the following settings: Capillary voltage 4000 V; cone voltage 30 V; RF Lens offset 0.38 V; source block temperature 80° C.; desolvation gas temperature 140° C.; desolvation gas 240 l/h; LM/HM Resolution 0.0; Collision energy 4.0 V; Ion energy 5.0 V.

Masses were monitored according to the known or expected M/Z ratios. Ion currents across the expected range of masses (including metabolites) were recorded and the chromatograms for specific masses used to estimate the peak area for a given molecular ion (area proportional to concentration over a given range). Normalization to DNA and/or protein and/or haem content of cells (all three measured with standard methods (Bisbenzimide staining (Sigma), BCA protein assay kit (Pierce) and haem absorbance at 535 nm, respectively)) to cell number (hemocytometer count) and cell volume was employed to calculate average compound concentration in the cell fraction (expressed in uM). Formation of metabolites or hydrolysis products was also monitored for each T-L-D conjugate and the rate of hydrolysis estimated from both the total uptake and the loss of metabolites to the medium. The final ratio was computed by comparing the concentration of a component in the immune cell compartment with that in both the erythrocytes and the plasma.

Example 12 hERG Inhibition by Compound 2 and 3

A major drawback of macrocycles is the inhibition of cardiac ion channels and specifically the channel encoded by the hERG gene inhibition of which is associated with "long Q-T" syndrome in some patients. To determine risk of hERG inhibition, Compounds 2 and 3 were incubated with Chinese hamster ovary cells expressing the hERG c-DNA resulting in detectable K+ currents associated with hERG at the cell surface. Compound 2 is a less potent inhibitor than the commercially available Compound 3 suggesting that Compound 2 should be safe for use in normal dose ranges.

Example 13

Cytotoxicty of the Substances

| | $TC_{50}$ | | |
|---|---|---|---|
| Compound | HeLa | Jurkat | HepG2 |
| 1 | | | |
| 2 | >100 | 40 | 90 |
| 3 | >100 | >100 | |
| 4 | >100 | >100 | |
| 5 | | >100 | |

Example 14

Mutagenicity

The Ames test is well known in the art. To determine the mutagenic potential of compound 2, it was conducted up to a concentration of 800 µg/plate (approx. 70 µM, considering 20 ml medium in a petri dish). Compound 2 showed no mutagenic activity in the absence and presence of metabolically active liver extract respectively.

Example 15

Activity of Compound 2 in an Arthritis Model

The data are obtained using the collagen arthritis model. Male DBA mice (18-22 g) are subcutaneously injected at the tail base with bovine type II collagen (100 µL) on day 1 and day 21. Onset of arthritis occurs over the next 5 days. Treatments are typically selected from A) a mixture of a Compound such as Compound 2 (between 2 to 40 µmol kg$^{-1}$) and the vehicle which is typically 1% citric acid in water or similar. The effect of treatment on arthritis is monitored daily by assessing body weight, paw thickness and qualitative evidence of arthritis (scored from 0 to 3, 0=no evidence of arthritis or inflammation, 3=frank swelling of the paw). At the end of qualitative assessment, animals are sacrificed for toxicological, histological and pathological analysis. Compound 2 when administered to the animals prior to or at the start of arthritis, exerts reductions in score, paw swelling and reduces loss in body weight associated with arthritis. Example data from treatment of an arthritis model are indicated in FIG. 4.

Example 16

Antibacterial Effects

The antibiotic activity of the compounds was determined via antibiotic dilution assay. After filling 100 µl growth medium into all the wells of a 96 well plate, the compounds were diluted from 1 mM to 0.010 µM. The growth control wells contained growth medium instead of inhibitory agents. The inhibitory control contained Compound 3 (200 µM). Suspensions of E. coli and B. pumilus in growth medium with an approximate OD600 of 0.03-0.04 were added to the diluted compounds, incubated for 6-8 hours on the shaker at 750 rpm and 37° C. until the growth control had reached an OD600 of about 0.6-0.8. The OD600 was then determined on a standard plate reader.

Example 17

Lack of Toxicity in Compound 2

To determine the potential for toxic effects of compound 2 in higher animals, compound 2 was administered to bALBc mice orally as a suspension up to a dose of 400 µmole/kg/day for 7 days. Animals continued to gain weight during this period suggesting no gross toxic effect.

Exposure to the compound was confirmed using LCMS analysis of organs. Compound 2 is slightly accumulated in kidney, liver and spleen. A mild increase in Compound 2 concentration relative the average bodily dose in liver and spleen is clear after 2 h. In kidney the increase appears later, after 24 h. Within this period more than 50% of the initial value can be detected indicating that at the dosing regime illustrated, very high exposure was achieved without toxic effect.

Example 18

Upscaling Procedure for Compound 2

A stirred solution of 12 ml (142 mmol) of oxalyl chloride in dry dichloromethane (400 ml) under Argon was chilled to −72° C.±5° C. in an acetone-dry ice-bath and 16 ml (225 mmol) dimethyl sulfoxide were added slowly (30 min total addition time) through an addition funnel. Initially, vigorous gas evolution was observed with every drop. The solution was stirred at −72° C.±5° C. for 20 min, then a solution of Compound 1 (20 g, dried for 3 hours in high vacuum at 60° C.) in dry dichloromethane (120 ml) was added slowly (40 min total addition time) through an addition funnel. The colorless suspension was kept at −72° C.±5° C. for 1 hour. At which point, 40 ml (237 mmol) of dry ethyl diisopropylamine were added slowly (30 min total addition time) through an addition funnel which produced a clear yellowish solution. The reaction mixture was stirred for another 20 min at −72° C.±5° C., which was followed by addition of 50 ml methanol in portion. The solution was kept at −72° C.±5° C. for another 10 min, before allowing to reach room temperature.

After which, the reaction mixture was transferred into a separation funnel and the reaction flask washed with additional dichloromethane (150 ml). The combined organic layers were washed with saturated bicarbonate twice (400 ml each) and one time with brine (400 ml). The organic layer was dried over sodium sulfate and evaporated under reduced pressure.

Methanol (300 ml) was added to the yellow foam and the solution was stirred at room temperature over night. The solvent was removed under reduced pressure and the yellow oil taken up into 500 ml of ethyl acetate. The organic layer was extracted with 500 ml 1N sodium hydroxide/brine (1:1), dried over sodium sulfate. Toluene (200 ml) were added and the solution concentrated to 35 ml. Crystallization already starts on concentration. In order to complete the precipitation the suspension was kept at −20° C. over night.

Yield: 10.5 g (57%) colorless powder, Compound 2.

Example 19

Activity of Compound 2 and Analogs in Models of Inflammatory Bowel Disease

Dextransulfate (DSS) is used to induce an inflammatory state in the gut of mice by providing it in the drinking water. In our model, DSS (ICN) was used at 2.5% W/V in drinking water for female C57BLK6 mice (ca. 20 g). Weight was monitored daily as were diarrhea, overall condition and occult blood. Depending on severity, animals were recovered at 5, 7 or 12 days after onset of DSS treatment, and colon and intestine material recovered for histological examination. Histology revealed the estent of lesions, the degree to which the laminapropia is compromised and the nature of infiltrating cells. Compound 2, relative to known compounds such as sulfasalazine, provided reductions in diarrhea severity, protection against weight loss, and reduced mortality (FIGS. 5 and 6). The effect of compound 2 in the DSS model relative to sulfasalazine or compounds 4 and 6 is indicated in FIGS. 10 and 11.

Example 20

Activity of Compound 2 and Analogs in Models of Inflammatory Bowel Disease Based on Trinitrobenzene Sulphonic Acid Trinitrobenzene sulphonic acid (TNBS) is used to induce an inflammatory state in the colon of mice by providing it via the intra rectal route in 50% ethanol water in the range of 2 mg/mouse. Administered in this way, TNBS causes weight loss, diarrhea and inflammation of the colon. It is widely considered that the reaction consists of an acute and T-cell mediated response at the level of the colonic mucosa. To determine effects of compounds in this model, weight and diarrhea was monitored daily and the colon and intestine material were recovered on sacrifice for scoring and determination of cytokines. The effect of Compound 2 at 26 mg/kg p.o. in the TNBS model is described in FIG. 7.

Example 21

Nitrooxide Variant of Compound 2

The compound CSY 0073 (1 equiv.) is dissolved in acetic acid (approximately 6.0 ml per 1 mmol compound) and a solution of nitric acid (10% in acetic anhydride, about 3.25 ml per 1 mmol compound) is slowly added to the system while cooling in an ice bath. When TLC indicates complete consumption of starting materials the mixture is poured onto ice hydrolyzing any remains of acetic anhydride, followed by cautious neutralization of acid species with sodium bicarbonate. Extraction of the aqueous system with dichloromethane (3×), drying of combined organic phases over sodium sulfate and subsequent purification of crude products by column chromatography (acetone-cyclohexane 1:3→1:1) yielded the product as amorphous white foam.

Example 22

Compound 8

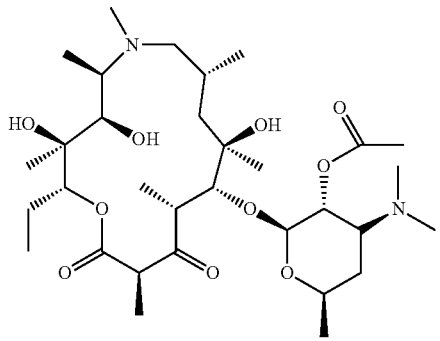

To a stirred solution of 300 mg Compound 2 (0.51 mmol) in dry dichloromethane (3.0 ml) was added at room temperature 51 µL acetic anhydride (0.53 mmol) in one portion. The reaction mixture was stirred at room temperature overnight. Then potassium carbonate was added and stirring continued for 20 min. The solid was filtered off and washed with dichloromethane (20 ml). The combined filtrates were evaporated to dryness.

The crude product was purified by column chromatography (Silica gel 60, 0.04-0.063 mm; eluent: Chloroform/2-Propanol/Ammonia in Methanol (7 M) 30:1:1) to yield 188 mg of the title compound as a colorless solid.

Example 23

Compound 9

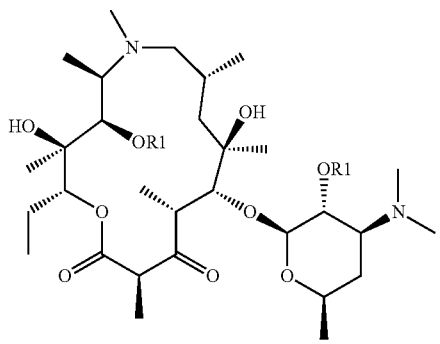

R1 = oleic ester

To a stirred solution of 200 mg Compound 2 (0.0, 34 mmol) in dry dichloromethane (2.0 ml) were added at room temperature under argon atmosphere 130 mg 1-Ethyl-3-(3-dimethylaminopropyl)carbodiimide hydrochloride (0.68 mmol) and 4-dimethylaminopyridine (catalytic amount). The mixture was stirred at room temperature for 10 min. Then 115 (129 µL) mg oleic acid (0.68 mmol) was added in one portion. Stirring at room temperature was continued overnight. Afterwards sodium bicarbonate solution (sat.) was added, and stirring continued for 10 min. Dichloromethane was added; after extraction the organic phase was washed with brine (1×), dried (sodium sulfate), and concentrated to dryness to give a colorless oil. The crude product was purified by column chromatography (silica gel 60, 0.04-0.063 mm; eluent: chloroform/2-propanol/ammonia in methanol (7 M) 30:1:1) to yield Monooleate ester—example 9a (79 mg) and di-oleate ester, example 9b (40 mg) as colorless oils.

Example 24

Compound 10

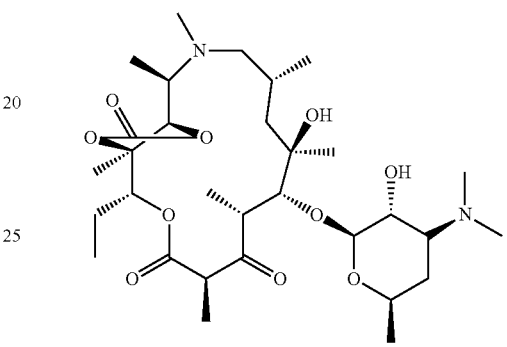

10.0 g of ethylene carbonate (113 mmol) was heated to 70° C. At this temperature 500 mg of Compound 2 (0.85 mmol) was added and the mixture was stirred at that temperature for 48 h. Afterwards the mixture was allowed to cool down for 10 min before ethyl acetate and water were added. After extraction the organic phase was dried (sodium sulfate) and concentrated in vacuo. The crude product was purified by column chromatography (silica gel 60, 0.04-0.063 mm; eluent: chloroform/2-propanol/ammonia in methanol (7 M) 30:1:1) to yield CSY 2239 (82 mg).

Example 25

Compound 11

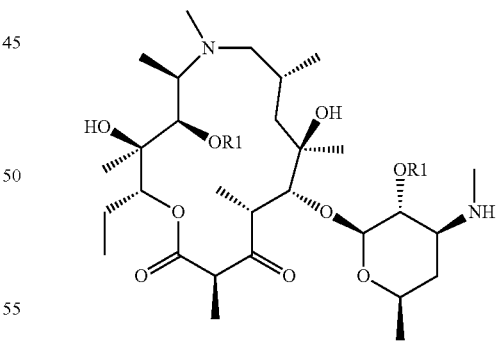

To a suspension of 392 mg Compound 2 (0.67 mmol) in acetonitrile (12.5 ml) was added 375 mg of N-iodosuccinimide (1.67 mmol) in one portion at room temperature. After two minutes as much saturated sodium sulfite solution was added as was necessary to get an almost colorless reaction mixture. The mixture was concentrated in vacuo and the residue portioned between dichloromethane and water. The aqueous phase was extracted with dichloromethane two more times; the combined organic phases were washed with saturated sodium bicarbonate solution, dried with sodium sulfate and concentrated to dryness.

The crude product was purified by column chromatography (silica gel 60, 0.04-0.063 mm; eluent: [chloroform/2-propanol/ammonia in methanol (7 M) 30:1:1)]/methanol 7:3 to yield CSY 7000 (37 mg).

Example 26

Compound 12, Triacetylated Compound 2

To a stirred solution of 300 mg Compound 2 (0.51 mmol) in dry dichloromethane (3.0 ml) was added at room temperature 510 µL, of acetic anhydride (5.3 mmol) in one portion. The reaction mixture was stirred at room temperature for 120 h. Sodium bicarbonate solution (sat.) was added and the mixture was stirred for 5 min. DCM and more sodium bicarbonate solution (sat.) are added. After extraction the organic phase is dried (sodium sulfate) and concentrated in vacuo. The crude product was purified by column chromatography (Silica gel 60, 0.04-0.063 mm; eluent: Chloroform/2-Propanol/Ammonia in Methanol (7 M) 30:1:1) to yield 230 mg of the title compound as a colorless oil.

Example 27

Compound 13

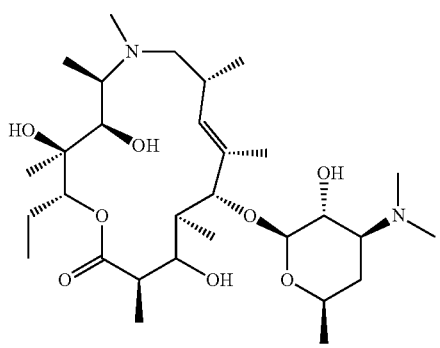

2.72 g of Compound 1 (0.43 mmol) was taken up in absolute pyridine (15 ml). To this was added 1.05 g of methanesulfonic anhydride (0.6 mmol, 1.4 eq.). Reaction progress was monitored by MS. Pyridine was evaporated in vacuo and the residue dissolved in dichloromethane followed by extractive workup with sodium bicarbonate solution.

The product obtained was dissolved in DMF (10 ml) and THF (3 ml). To this was added 294 mg of NaH (60% in mineral oil, 12.25 mmol) at 0° C. After 3 h, reaction was complete based on MS. Reaction was allowed to warm to room temperature where it was subjected to an acid-base workup to get Compound 13 as a light brown product (850 mg).

Example 28

Alternative Procedure for Compound 11 and by-Product Compound 14

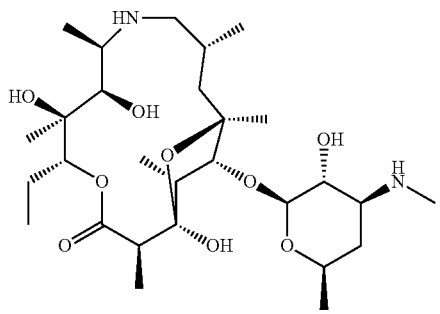 [SMILES: CC[C@H]1OC(=O)[C@H](C)[C@@]2(O)O[C@@](C)(C[C@@H](C)CN[C@H](C)[C@@H](O)[C@]1(C)O)[C@H](O[C@@H]1O[C@H](C)C[C@H](NC)[C@H]1O)[C@H]2C]

3.2 g (5.4 mmol) Compound 2 was dissolved in a methanolic solution of NaOH (5.25 g, 0.13 mol in 100 ml MeOH). 1.78 g (6.8 mmol) iodine was added while stiffing. After 2 h 200 µL water was added and stirring was continued over night. Then the solution was evaporated and the residue subjected to column chromatography (200 g silica gel; Cyclohexane/Acetone, 3/1) to yield 760 mg of Compound 11 and 730 mg of Compound 14 as a white powder (M/Z=561 (M+H)).

Example 29

Compound 15

To a stirred solution of 1.0 g compound 2 (1.7 mmol) in dry dichloromethane (6.0 ml) were added at room temperature 250 mg of 4-dimethylaminopyridin (2.05 mmol) and 2.0 g of carbonyldiimidazole (12.33 mmol). The mixture was stirred at room temperature for 30 minutes. Dichloromethane and sodium bicarbonate solution (sat.) were added; after extraction the organic phase was dried (sodium sulfate) and concentrated in vacuo.

The crude product was purified by column chromatography (Silica gel 60, 0.04-0.063 mm; eluent: Chloroform/2-Propanol/Ammonia in Methanol (7 M) 30:1:1) to yield 590 mg of compound 15 (M/Z=763 (M+H)).

Example 30

Liver Inflammation

Animals habituated to 8% ethanol in drinking water exhibit susceptibility to liver inflammation following exposure to bacterial toxins such as lipopolysaccharide. Application of high doses of LPS, e.g. 4 mg/kg i.p. results in the induction of liver inflammation and necrosis. This is reflected in signs such as elevated plasma TNFalpha levels. The effect of Compound 2 applied at either 10 or 50 mg/kg is to reduce plasma TNF levels relative to vehicle treated controls. Data are recorded in FIG. 12.

Example 31

In Vitro/In Vivo Profiling

Various analogs were compared in vitro to determine key properties. Antibacterial effect was determined in representative Gram negative (*E. coli*) and positive (*S. aureus*) organisms using the method of example 16. Effects on lung inflammation were compared using the method of example 32. BALF (Bronchoalveolar Lavage Fluid) TNFa levels are determined by ELISA. In vitro toxicity is determined by growth inhibition of Jurkat lymphocytes in DMEM medium as determined using Alamar Blue reaction. Effects on cytokine production are determined in J774 cells stimulated with either LPS (0.1 µg/mL) or medium from J774 cells stimulated for 24 h with 0.2 µg/mL LPS. Cytokines are determined by ELISA and expressed as % DMSO control at 50 µM inhibitor concentration.

The results are shown in Table 1:

TABLE 1

| Compound Example # | Bacterial IC 50 (μM) | | BALF TNFa (% Vehicle) | | Jurkat Cell toxicity | Cytokine production in J774 cells as % DMSO control | | | |
|---|---|---|---|---|---|---|---|---|---|
| | | | 20 μmol/kg | 200 μmol/kg | Normal growth limit | TNFa Normal | GM_CSF Cond. | IL-10 Normal | IL-12 Normal |
| | E. Coli | S. Aureus | i.n. | p.o. | (μM) | 50 μM | 50 μM | 50 μM | 50 μM |
| 3 | 5.5 | 2.25 | 75 | | 100 | 96 | 118 | 122 | 60 |
| 2 | 1000 | 1340 | 75 | | 100 | 68 | 160 | 115 | 42 |
| 5 | 980 | 2600 | 90 | | 100 | 39 | 114 | 95 | 7 |
| 5a | 1420 | 1920 | 110 | 70 | 100 | 91 | 71 | 119 | 72 |
| 5b | 1090 | 1920 | 56 | | 100 | 88 | 81 | 116 | 67 |
| 8 | 1270 | 1970 | 81 | 67 | 100 | 85 | 83 | 134 | 45 |
| 9a | 5000 | 5000 | | | 12 | 15 | 37 | 116 | 24 |
| 9b | 1950 | 2500 | 112 | | 100 | 89 | 53 | 123 | 76 |
| 10 | 1350 | 1600 | 99 | | 100 | 72 | 14 | 118 | 40 |
| 11 | 1090 | 2340 | 80 | 98 | 100 | 86 | 174 | 96 | 53 |
| 13 | 2140 | 1570 | 78 | | 100 | 99 | 193 | 98 | 47 |
| 14 | 1320 | 1950 | 62 | 95 | 100 | 93 | 153 | 95 | 143 |
| 14b | 900 | 1550 | 72 | | 100 | 76 | 185 | 94 | 32 |
| 26 | 1430 | 1870 | 75 | | 100 | 89 | 24 | 119 | 64 |
| 29 | 2610 | 2650 | 95 | | 100 | 90 | 42 | 117 | 68 |

Example 32

Activity of Compound 2 in Airway Inflammation

Airway inflammation is induced by inhalation of solutions containing bacterial LPS. 10 μg per mouse is provided intranasally in phosphate buffered saline. 90 minutes after challenge, bronchioalveolar lavage fluid is recovered from the lung using PBS (0.5 mL) injected into the lung via the trachea and frozen prior to analysis for cytokines by ELISA. TNFa is the primary cytokine measured. Compound 2 and other test substances are dissolved in 0.02% citric acid in water, and the pH of the resulting solution is set to 6.2. Compounds are administered 30 minutes prior to challenge either as 25 μL solutions for intranasal use, or as 125 μL volumes for p.o. application in 25 g DBA or Swiss female mice. The results of said interventions include reduction of lung and/or plasma cytokines. Example data are recorded in FIG. 13.

What is claimed is:

1. A compound of the following formula:

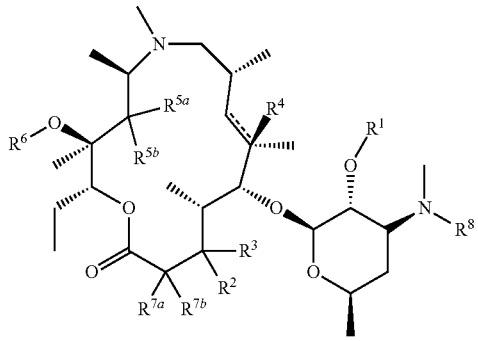

Wherein:
The dashed line represents an optional bond;
$R^1$ is H and $R^8$ is independently H or $CH_3$;
$R^2$ and $R^3$=—OH (provided that only one of $R^2$ and $R^3$ is OH and the other is H);
or $R^2$ and $R^3$ taken together are (=O);
or $R^2$=OH, and $R^3$ and $R^4$ taken together with the carbon atoms to which they are attached, form a 5- or 6-membered oxygen-containing ring;
$R^4$=absent; provided that when $R^4$ is absent, the dashed line represents a bond;
$R^{5a}$=H, $R^{5b}$=OH
$R^6$=H;
$R^{7a}$=H;
and
$R^{7b}$= $CH_3$;
or a pharmaceutically acceptable salt thereof.

2. A method for producing a compound of claim 1, the method comprising the step of oxidizing a descladinosyl macrocyclic compound of claim 1 wherein one of $R^2$ and $R^3$ is OH to form a compound of claim wherein $R^2$ and $R^3$ taken together are (=O).

3. The method of claim 2, in which the step of oxidizing comprises oxidizing using the Swern reaction.

4. A pharmaceutical composition comprising a compound or pharmaceutically acceptable salt of claim 1 and a pharmaceutically acceptable carrier.

5. A method of treating an inflammatory disorder, the method comprising administering to a subject in need thereof an effective amount of a compound or pharmaceutically acceptable salt of claim 1.

6. A method of manufacturing a pharmaceutical composition, the method comprising mixing a compound or pharmaceutically acceptable salt of claim 1 with a suitable pharmaceutically acceptable carrier.

7. A compound that is 11-(4-Dimethylamino-3-hydroxy-6-methyl-tetrahydro-pyran-2-yloxy)-2-ethyl-3,4,10-trihydroxy-3,5,6,8,10,12,14-heptamethyl-1-oxa-6-aza-cyclopentadecane-13,15-dione.

8. The compound of claim 1, that is selected from:

Compound 2

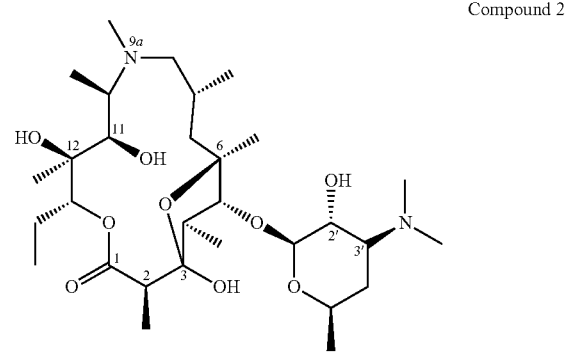

-continued
Compound 13
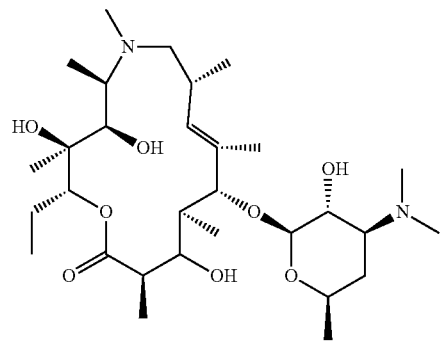
Compound 14
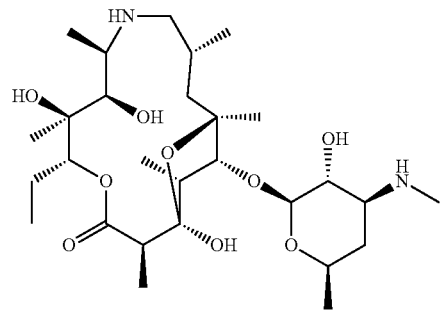
or pharmaceutically acceptable salt thereof.
* * * * *